(12) United States Patent
Mezaache et al.

(10) Patent No.: US 7,815,937 B2
(45) Date of Patent: Oct. 19, 2010

(54) QUICK DISSOLVE COMPOSITIONS AND TABLETS BASED THEREON

(75) Inventors: Naima Mezaache, McLean, VA (US); Steven E. Frisbee, Reston, VA (US); Patrick B. Woodall, Culpeper, VA (US); Mark R. Herman, Nokesville, VA (US); Djelila Mezaache, Aldie, VA (US)

(73) Assignee: Biovail Laboratories International SRL, St. Michael (BB)

( * ) Notice: Subject to any disclaimer, the term of this patent is extended or adjusted under 35 U.S.C. 154(b) by 207 days.

(21) Appl. No.: 10/176,135

(22) Filed: Jun. 21, 2002

(65) Prior Publication Data
US 2003/0124184 A1 Jul. 3, 2003

Related U.S. Application Data

(63) Continuation-in-part of application No. 09/179,926, filed on Oct. 27, 1998, now abandoned.

(51) Int. Cl.
*A61K 9/20* (2006.01)
(52) U.S. Cl. ...................... 424/465; 424/458
(58) Field of Classification Search .............. 424/464, 424/465, 484, 458
See application file for complete search history.

(56) References Cited

U.S. PATENT DOCUMENTS

| | | | |
|---|---|---|---|
| 4,017,598 A | 4/1977 | Ohno et al. | |
| 4,517,179 A * | 5/1985 | Raghunathan | 514/249 |
| 5,073,374 A | 12/1991 | McCarty | |
| 5,160,680 A * | 11/1992 | Serpelloni et al. | 264/126 |
| 5,204,115 A * | 4/1993 | Olinger et al. | 424/470 |
| 5,464,632 A * | 11/1995 | Cousin et al. | 424/465 |
| 5,536,526 A * | 7/1996 | Virtanen et al. | 426/658 |
| 5,587,180 A | 12/1996 | Allen, Jr. et al. | |
| 5,683,720 A * | 11/1997 | Myers et al. | 424/489 |
| 5,762,961 A | 6/1998 | Roser et al. | |
| 5,849,223 A | 12/1998 | Myers et al. | |
| 5,851,555 A | 12/1998 | Sanghvi et al. | |
| 5,871,781 A | 2/1999 | Myers et al. | |
| 5,876,759 A | 3/1999 | Gowan, Jr. | |
| 5,965,167 A | 10/1999 | Sanghvi et al. | |
| 5,980,941 A | 11/1999 | Raiden et al. | |
| 6,024,981 A * | 2/2000 | Khankari et al. | 424/464 |
| 6,083,430 A | 7/2000 | Fuisz et al. | |
| 6,086,920 A | 7/2000 | Frisbee et al. | |
| 6,106,861 A | 8/2000 | Chauveau et al. | |
| 6,117,452 A | 9/2000 | Ahlgren et al. | |
| 6,149,938 A | 11/2000 | Bonadeo et al. | |
| 6,165,512 A | 12/2000 | Mezaache et al. | |
| 6,221,392 B1 | 4/2001 | Khankari et al. | |
| 6,316,029 B1 | 11/2001 | Jain et al. | |
| 6,468,959 B1 | 10/2002 | Wunderlich et al. | |
| 6,497,899 B2 | 12/2002 | Thombre et al. | |
| 6,500,456 B1 | 12/2002 | Capella | |
| 6,596,311 B1 | 7/2003 | Dobetti | |
| 6,602,520 B1 | 8/2003 | Schroeder et al. | |
| 6,692,771 B2 | 2/2004 | Pather et al. | |
| 6,696,085 B2 | 2/2004 | Rault et al. | |
| 6,733,781 B2 | 5/2004 | Abu-Izza et al. | |
| 6,872,405 B2 | 3/2005 | Takaishi et al. | |
| 7,118,765 B2 | 10/2006 | Norman et al. | |
| 7,208,175 B2 | 4/2007 | Schroeder et al. | |
| 7,255,876 B2 | 8/2007 | Shinoda et al. | |
| 2002/0071864 A1 | 6/2002 | Kim et al. | |
| 2002/0076437 A1 | 6/2002 | Kothari et al. | |
| 2002/0114833 A1 | 8/2002 | Abu-Izza et al. | |
| 2002/0168404 A1 | 11/2002 | Rault et al. | |
| 2003/0022912 A1 | 1/2003 | Martino et al. | |
| 2003/0077306 A1 | 4/2003 | Pather et al. | |
| 2003/0124184 A1 | 7/2003 | Mezaache et al. | |
| 2003/0147947 A1 | 8/2003 | Serpelloni | |
| 2003/0161875 A1 | 8/2003 | Murpani et al. | |
| 2004/0037878 A1 | 2/2004 | Szamosi et al. | |
| 2004/0057993 A1 | 3/2004 | Jain et al. | |
| 2004/0137060 A1 | 7/2004 | Fogarty et al. | |
| 2006/0165781 A1 | 7/2006 | Ferran | |
| 2007/0048378 A1 * | 3/2007 | Swanson et al. | 424/469 |

FOREIGN PATENT DOCUMENTS

JP 70264583 A * 3/1997

(Continued)

OTHER PUBLICATIONS

Yoko Yamada, et al., "Preparation and Evaluation of Rapidly Disintegrating Tablets in the Oral Cavity by the Dry Compression Method," Faculty of Pharmacy, vol. 66 (6), 473-481 (2006).

(Continued)

*Primary Examiner*—Johann R Richter
*Assistant Examiner*—Ali Soroush
(74) *Attorney, Agent, or Firm*—Oblon, Spivak, McClelland, Maier & Neustadt, L.L.P

(57) ABSTRACT

The invention provides a composition useful for making oral dosage forms capable of dissolving in the mouth in less than 40 seconds without the need for a conventional super disintegrant and having a friability of less than 1%; wherein the composition includes liquiflash particles and an excipient mass. A preferred excipient mass according to the invention contains a directly compressible inorganic salt; a cellulose derivative or a combination of a directly compressible inorganic salt and a cellulose derivative. Preferably, the liquiflash particles and the excipient mass are combined in proportions such that the active ingredient remains substantially within the microspheres when the composition is compressed to obtain a dosage form having a hardness of 20 to 50 N. The compositions of the invention allow for the fabrication of oral dosages having improved hardness and friability.

48 Claims, No Drawings

FOREIGN PATENT DOCUMENTS

| WO | WO 99/17743 | 4/1999 |
| --- | --- | --- |
| WO | WO 00/24380 | 5/2000 |
| WO | WO 00/51568 | 9/2000 |
| WO | WO 01/87264 | 11/2001 |
| WO | WO 02/062315 | 8/2002 |
| WO | WO 02/067894 | 9/2002 |
| WO | WO 02/083102 | 10/2002 |
| WO | WO 03/026610 | 4/2003 |
| WO | WO 03/030876 | 4/2003 |
| WO | WO 03/051338 | 6/2003 |
| WO | WO 03/103629 | 12/2003 |

OTHER PUBLICATIONS

Atsuhi Watanabe, et al., "New Oral Dosage Form for the Elderly," Yakuzaigaku, 52 (2), pp. 103-110 (1994).

Toshifusa Shu, et al., "Studies of Rapidly Disintegrating Tablets in the Oral Cavity Using Co-ground Mixtures of Mannitol with Crospovidone," Chem. Pharm. Bull., 50 (2), 193-198 (2002).

S.R. Parakh, et al., "A Review of Mouth Dissolving Tablets Technologies," Pharmaceutical Technology, Nov. 2003.

Takao Oshima, et al., "Wet-Compressed Rapidly Disintegrating Tablets in the Oral Cavity Containing High-Content Poorly Water-Soluble Model Drug," Faculty of Pharmacy, 63 (1), 1-11 (2003).

Shagufta Khan, et al., "Taste Masking of Ondansetron Hydrochloride by Polymer Carrier System and Formulation of Rapid-Disintegrating Tablets," AAPS PharmSciTech, 8 (2), Article 46 (2007).

Mukesh Gohel, et al., "Formulation Design and Optimization of Mouth Dissolve Tablets of Nimesulide Using Vacuum Drying Technique," AAPS PharmSciTech, 5 (3), Article 36 (2004).

Yunxia Bi, et al., "Preparation and Evaluation of a Compressed Tablet Rapidly Disintegrating in the Oral Cavity," Chem. Pharm. Bull, 44 (11) 121-127 (1996).

Masaaki Sugimoto, et al., "The Preparation of Rapidly Disintegrating Tablets in the Mouth," Pharmaceutical Development and Technology, 6 (4), 487-493 (2001).

Jin Y., et al. "Pharmaceutical Evaluation of Fast-Disintegrant Tablet Containing Nicorandil-Loaded Particles," Yao Xue Xue Bao, Jul. 2001 36 (7): 535-8.

Watanabe, Y et al., "New Compressed Tablet Rapidly Disintegrating in Saliva in the Mouth Using Crystalline Cellulose and a Disintegrant," Bio Pharm Bull., Sep. 1995; 18(9): 1308-10.

* cited by examiner

QUICK DISSOLVE COMPOSITIONS AND TABLETS BASED THEREON

RELATED APPLICATIONS

The present application is a continuation in part of U.S. application Ser. No. 09/179,926 filed Oct. 27, 1998, now abandoned the content of which are hereby incorporated by reference in their entirety.

FIELD OF THE INVENTION

The invention relates to compressible compositions and dosage forms based thereon, such as tablets and lozenges, which, when ingested, quickly dissolve in the mouth, but which effectively mask the taste of unpleasant active agent(s) therein. Also, the invention relates to readily processable compositions having enhanced friability and hardness properties which permit shaping, e.g., tableting, without the need for complex packaging equipment.

BACKGROUND

The post-genomics phase in the life sciences arena has brought an increased yield of new small molecules that are pursued to target particular diseases based on the new understanding of the molecular basis of disease. The tremendous progress achieved in molecular structural biology has allowed the identification and de novo design of efficient molecules or so called "smart drugs." The new technologies based on the unraveling of the human genome, the intensive progress in elucidating the structures of the enzymes encoded therein combined with the efficiencies of combinatorial chemistry will continue to generate small molecules that need to be administered to patients in efficient and organoliptically acceptable forms. One aspect associated with ameliorating the effects of ingesting molecules that are generally unpalatable is to provide the drug in dosage forms, such as tablets and lozenges, which, when ingested, quickly dissolve in the mouth.

Tablets may be defined as solid dosage pharmaceutical forms containing drug substances with or without suitable fillers. They are produced by compression or compaction of a formulation containing the drug and certain excipients selected to aid in the processing and to improve the properties of the product. Tablets may be coated or uncoated and are made from powdered, crystalline materials. They may include various diluents, binders, disintegrants, lubricants, glidants and in many cases, colorants. Excipients used are classified according to the function they perform. For example, a glidant may be used to improve the flow of powder blend in the hopper and into the tablet die.

There has been widespread use of tablets since the latter part of the 19.sup.th century and the majority of pharmaceutical dosage forms are marketed as tablets. Major reasons of tablet popularity as a dosage form among pharmaceutical manufacturers are simplicity, low cost, and the speed of production. Other reasons include stability of drug product, convenience in packaging, shipping, and dispensing. To the patient or consumer, tablets offer convenience of administration, ease of accurate dosage, compactness, portability, blandness of taste, ease of administration, and elegant distinctive appearance.

Tablets may be plain, film or sugar coated, bisected, embossed, layered, or sustained release. They can be made in a variety of sizes, shapes and colors. Tablets may be swallowed, chewed, or dissolved in the buccal cavity or beneath the tongue. They may be dissolved in water for local or topical application. Sterile tablets are normally used for parenteral solutions and for implantation beneath the skin.

In addition to the active or therapeutic ingredients, tablets may contain a number of inert materials known as excipients. They may be classified according to the role they play in the final tablet. The primary composition includes a filler, binder, lubricant, and glidant. Other excipients which give physical characteristics to the finished tablet are coloring agents, and flavors in the case of chewable tablets. Without excipients most drugs and pharmaceutical ingredients cannot be directly compressed into tablets. This is primarily due to the poor flow and cohesive properties of most drugs. Typically, excipients are added to a formulation to impart good flow and compression characteristics to the material being compressed. Such properties are imparted to these excipients through pretreatment steps such as wet granulation, slugging, spray drying spheronization, or crystallization.

Lubricants are typically added to prevent the tableting materials from sticking to punches, minimize friction during tablet compression, and allow for removal of the compressed tablet from the die. Such lubricants are commonly included in the final tablet mix in amounts usually less than 1% by weight.

In addition, tablets often contain diluents which are added to increase the bulk weight of the blend resulting in a practical size for compression. This is often necessary where the dose of the drug is relatively small.

Another commonly used class of excipients in tablets is binders. Binders are agents, which impart cohesive qualities to the powdered material. Commonly used binders include starch, and sugars such as sucrose, glucose, dextrose, and lactose.

Disintegrants are often included to ensure that the tablet has an acceptable rate of disintegration. Typical disintegrants include starch derivatives and salts of carboxymethylcellulose.

Other desirable characteristics of excipients include the following:

High compressibility to allow strong tablets to be made at low compression forces.

Good flow properties that can improve the flow of other excipients in the formula.

Cohesiveness (to prevent tablet from crumbling during processing, shipping and handling).

The three processes for making compressed tablets are wet granulation, direct compression, and dry granulation (slugging or roller compaction). The method of preparation and type of excipients are selected to give the tablet formulation the desired physical characteristics that allow for the rapid compression of the tablets. After compression, the tablets must have a number of additional attributes such as appearance, hardness, disintegrating ability, and an acceptable dissolution profile. Choice of fillers and other excipients will depend on the chemical and physical properties of the drug, behavior of the mixture during processing, and the properties of the final tablets. Preformulation studies are done to determine the chemical and physical compatibility of the active component with proposed excipients.

The properties of the drug, its dosage forms, and the economics of the operation will determine selection of the best process for tableting. Generally, both wet granulation and direct compression are used in developing a tablet.

The dry granulation method may be used where one of the constituents, either the drug or the diluent, has sufficient cohesive properties to be tabled. The method consists of blending, slugging the ingredients, dry screening, lubrication, and compression.

The wet granulation method is used to convert a powder mixture into granules having suitable flow and cohesive properties for tableting. The procedure consists of mixing the powders in a suitable blender followed by adding the granulating solution under shear to the mixed powders to obtain a granulation. The damp mass is then screened through a suitable screen and dried by tray drying or fluidized bed drying. Alternately, the wet mass may be dried and passed through a mill. The overall process includes: weighing, dry powder blending, wet granulating, drying, milling, blending lubrication and compression.

In general, powders do not have sufficient adhesive or cohesive properties to form hard, strong granules. A binder is usually required to bond the powder particles together due to the poor cohesive properties of most powders. Heat and moisture sensitive drugs cannot usually be manufactured using wet granulation. The large number of processing steps and processing time are problems due to high level manufacturing costs. Wet granulation has also been known to reduce the compressibility of some pharmaceutical excipients such as microcrystalline cellulose.

Direct compression is regarded as a relatively quick process where the powdered materials are compressed directly without changing the physical and chemical properties of the drug. The active ingredient(s), direct compression excipients and other auxiliary substances, such as a glidant and lubricant are blended in a twin shell blender or similar low shear apparatus before being compressed into tablets. This type of mixing was believed to be essential in order to prepare "pharmaceutically acceptable" dosage forms. For example, Remington's Pharmaceutical Sciences (RPS), pp 1203 to 1932 17.sup.th edition (1985), cautions pharmaceutical scientists that the manner in which a lubricant is added to a formulation must be carefully controlled.

Accordingly, lubricants are usually added to a granulation by gentle mixing. RPS warns that prolonged blending of a lubricant with a granulation can materially affect hardness and disintegration time for the resulting tablets. Furthermore, Ansel et al (1995) Pharmaceutical Dosage Forms and Drug Delivery Systems, 6.sup.th Ed. p. 199, indicates that excessive blending of lubricants with the granulate ingredients cause water proofing of the granule and reduces tablet hardness or strength of the compressed tablet. For these reasons, high shear mixing conditions have not been used to prepare direct compression dosage forms.

The advantages of direct compression include uniformity of blend, few manufacturing steps involved, (i.e. the overall process involves weighing of powders, blending and compression, hence less cost), elimination of heat and moisture, prime particle dissociation, and physical stability.

In addition to the assignee of the subject application, Biovail Laboratories, current manufacturers of rapidly disintegrating or dissolving solid dose oral formulations include Cima Labs, Prographarm/Ethypharm, R. P. Scherer, and Yamanouchi-Shaklee. All of these manufacturers market different types of rapidly dissolving solid oral dosage forms.

Cima Labs markets OraSolv™, which is an effervescent direct compression tablet purportedly having an oral dissolution time of five to thirty seconds, and DuraSolv™, which is a direct compression tablet having a taste-masked active agent and a purported oral dissolution time of 15 to 45 seconds. Cima's U.S. Pat. No. 5,607,697, for "Taste Masking Microparticles for Oral Dosage Forms," describes a solid dosage form consisting of coated microparticles that disintegrate in the mouth. The microparticle core has a pharmaceutical agent and one or more sweet-tasting compounds having a negative heat of solution selected from mannitol, sorbitol, a mixture of an artificial sweetener and menthol, a mixture of sugar and menthol, and methyl salicylate. The microparticle core is coated, at least partially, with a material that retards dissolution in the mouth and masks the taste of the pharmaceutical agent. The microparticles are then compressed to form a tablet. Other excipients can also be added to the tablet formulation.

WO 98/46215 for "Rapidly Dissolving Robust Dosage Form," assigned to Cima Labs, is directed to a hard, compressed, fast melt formulation having an active ingredient and a matrix of at least a non-direct compression filler and lubricant. A non-direct compression filler is typically not free-flowing, in contrast to a direct compression (DC grade) filler, and usually requires additionally processing to form free-flowing granules.

Cima also has U.S. patents and international patent applications directed to effervescent dosage forms (U.S. Pat. Nos. 5,503,846, 5,223,264, and 5,178,878) and tableting aids for rapidly dissolving dosage forms (U.S. Pat. Nos. 5,401,513 and 5,219,574), and rapidly dissolving dosage forms for water soluble drugs (WO 98/14179 for "Taste-Masked Microcapsule Composition and Methods of Manufacture").

Prographarm/Ethypharm markets Flashtab™, which is a fast melt tablet having a disintegrating agent such as carboxymethyl cellulose, a swelling agent such as a modified starch, and a taste-masked active agent. The tablets have a purported oral disintegration time of under one minute (U.S. Pat. No. 5,464,632).

R. P. Scherer markets Zydis™, which is a freeze-dried tablet having an oral dissolution time of 2 to 5 seconds. Lyophilized tablets are costly to manufacture and difficult to package because of the tablets sensitivity to moisture and temperature. U.S. Pat. No. 4,642,903 (R. P. Scherer Corp.) refers to a fast melt dosage formulation prepared by dispersing a gas throughout a solution or suspension to be freeze-dried. U.S. Pat. No. 5,188,825 (R. P. Scherer Corp.) refers to freeze-dried dosage forms prepared by bonding or complexing a water-soluble active agent to or with an ion exchange resin to form a substantially water insoluble complex, which is then mixed with an appropriate carrier and freeze dried. U.S. Pat. No. 5,631,023 (R. P. Scherer Corp.) refers to freeze-dried drug dosage forms made by adding xanthan gum to a suspension of gelatin and active agent. U.S. Pat. No. 5,827,541 (R. P. Scherer Corp.) discloses a process for preparing solid pharmaceutical dosage forms of hydrophobic substances. The process involves freeze-drying a dispersion containing a hydrophobic active ingredient and a surfactant, in a non-aqueous phase; and a carrier material, in an aqueous phase.

Yamanouchi-Shaklee markets Wowtab™, which is a tablet having a combination of a low moldability and a high moldability saccharide. U.S. patents covering this technology include U.S. Pat. No. 5,576,014 for "Intrabuccally Dissolving Compressed Moldings and Production Process Thereof," and U.S. Pat. No. 5,446,464 for "Intrabuccally Disintegrating Preparation and Production Thereof."

Other companies owning rapidly dissolving technology include Janssen Pharmaceutica. U.S. patents assigned to Janssen describe rapidly dissolving tablets having two polypeptide (or gelatin) components and a bulking agent, wherein the two components have a net charge of the same sign, and the first component is more soluble in aqueous solution than the second component. See U.S. Pat. No. 5,807,576 for "Rapidly Dissolving Tablet;" U.S. Pat. No. 5,635,210 for "Method of Making a Rapidly Dissolving Tablet;" U.S. Pat. No. 5,595,761 for "Particulate Support Matrix for Making a Rapidly Dissolving Tablet;" U.S. Pat. No. 5,587,180 for "Process for Making a Particulate Support Matrix for Making a Rapidly Dissolving Tablet;" and U.S. Pat. No. 5,776,491 for "Rapidly Dissolving Dosage Form."

Eurand America, Inc. has U.S. patents directed to a rapidly dissolving effervescent composition having a mixture of sodium bicarbonate, citric acid, and ethylcellulose (U.S. Pat. Nos. 5,639,475 and 5,709,886).

L.A.B. Pharmaceutical Research owns U.S. patents directed to effervescent-based rapidly dissolving formulations having an effervescent couple of an effervescent acid and an effervescent base (U.S. Pat. Nos. 5,807,578 and 5,807,577).

Schering Corporation has technology relating to buccal tablets having an active agent, an excipient (which can be a surfactant) or at least one of sucrose, lactose, or sorbitol, and either magnesium stearate or sodium dodecyl sulfate (U.S. Pat. Nos. 5,112,616 and 5,073,374).

Laboratoire L. LaFon owns technology directed to conventional dosage forms made by lyophilization of an oil-in-water emulsion in which at least one of the two phases contains a surfactant (U.S. Pat. No. 4,616,047). For this type of formulation, the active ingredient is maintained in a frozen suspension state and is tableted without micronization or compression, as such processes could damage the active agent.

Takeda Chemicals Inc., Ltd. owns technology directed to a method of making a fast dissolving tablet in which an active agent and a moistened, soluble carbohydrate are compression molded into a tablet, followed by drying of the tablets.

Biovail Corporation (the parent of the assignee of the subject application) markets Flash Dose™, which is a direct compression tablet containing a processed excipient called Shearform™. Shearform™ is a floss type substance of mixed polysaccharides converted to amorphous fibers. U.S. patents describing this technology include U.S. Pat. No. 5,871,781 for "Apparatus for Making Rapidly Dissolving Dosage Units;" U.S. Pat. No. 5,869,098 for "Fast-Dissolving Comestible Units Formed Under High-Speed/High-Pressure Conditions;" U.S. Pat. Nos. 5,866,163, 5,851,553, and 5,622,719, all for "Process and Apparatus for Making Rapidly Dissolving Dosage Units and Product Therefrom;" U.S. Pat. No. 5,567,439 for "Delivery of Controlled-Release Systems;" and U.S. Pat. No. 5,587,172 for "Process for Forming Quickly Dispersing Comestible Unit and Product Therefrom."

One way to provide self-binding flowable formulations is to formulate using Shearform™ matrices or flosses. These matrices result when using certain processing techniques, such as the following: U.S. Pat. No. 5,587,172, incorporated herein by reference, discusses the use of flash heat techniques to produce sucrose-containing shearform flosses, which are then processed to yield quick-dissolving tablets.

The use of shearform matrices for forming comestible units is described in WO95/34290 (published Dec. 21, 1995) from co-assigned PCT application No. PCT/US95/07144, filed Jun. 6, 1995. This case discloses a quick dissolving tablet which is formed by: (1) using flash-flow technology to provide a shearform matrix; (2) combining the partially recrystallized shearform matrix with an additive to form flowable, compactible particulate blends; and (3) compacting the blends at relatively low pressures to produce dosage forms, such as tablets.

Additionally, PCT publication WO 95/34293 (published Dec. 21, 1995) from co-assigned PCT application No. PCT/US95/07194, filed Jun. 6, 1995, discloses a process and apparatus for making rapidly dissolving dosage forms by flash-flow processing. In this PCT application, a shearform matrix is formed by the flash-flow process, the shearform matrix is combined with an additive, and the matrix is molded to make a unit dosage form.

Co-owned U.S. patent application Ser. No. 08/915,068, filed Aug. 20, 1997, now U.S. Pat. No. 5,840,331; and Ser. No. 09/132,986, filed Aug. 12, 1998, now U.S. Pat. No. 6,048,541, describe tablet formulations derived from saccharide-based carriers in which the use of a unique combination of feedstock ingredients yields self-binding, flowable matrices and tablet compositions. This combination—which uses a blend of sugar alcohols, i.e., sorbitol and xylitol—is superior to glycerine in providing cohesive properties and flowability.

Shapeable, preferably tabletable, compositions derived from partially hygroscopic matrices containing these sugar alcohols are useful—in the presence of tableting aids and crystallization promoters—in both high- and low-pressure tableting processes. Tablets and other dosage forms, e.g., lozenges, made therefrom rapidly dissolve when placed in the mouth, generally in less than 30 seconds.

The production of microspheres containing active agent(s) is described in co-owned U.S. Pat. No. 5,683,720, incorporated herein by reference. The patent deals with the use of Liquiflash™ processing to spheronize compositions containing one or more active agents.

Co-owned U.S. Pat. No. 6,165,512 provides compositions and shaped oral dosage forms made therefrom having improved properties. Among those properties are improved processability before shaping and enhanced dissolution and taste-masking properties when the dosage forms are used. The compositions of the '512 patent are based on matrices, or flosses, which comprise at least one sugar alcohol, which matrices are generally considered "single floss" or "unifloss" systems. These systems are exemplified by xylitol-containing shearform matrixes, or flosses, containing a carrier and two or more sugar alcohols.

Various ingredients, such as coated microspheres containing active agent(s), are added, in suitable amounts, to the compositions of the present invention after the matrices are collected and chopped, but before they are shaped, e.g., by tabletting.

Highly useful dosage forms result when microspheres made from compositions containing active agents, solubilizers and spheronization aids are coated with taste-masking agents, then combined with flosses and conventional pharmaceutical ingredients. The resultant tablets enjoy the processing ease associated with the use of glycerine-free flosses and the taste and release properties associated with coated microspheres.

The above mentioned existing quick dissolve technologies present numerous limitations. The above mentioned Prographarm (Ethypharm) dosage forms require relatively high levels of super disintegrant which complicates their use and limits their friability and hardness thereby requiring specialized packaging. Similarly, the Cima dosage forms require effervescent excipients which also reduces their friability and hardness qualities. The R P Scherer, Yamanouchi and Takada technoligies employ complicated processing techniques (i.e. lyophilization, solvents with heat treatment or drying). Those techniques increase the cost associated with the formation of the dosage forms on a large scale.

While Shearform™ matrices are an advance in the art, they also involve an increased cost associated with the processing of the floss matrix which limits their use at a large scale. As well, these amorphous matrices require specialized robotic tableting equipment and generally do not provide friability and hardness properties required for bulk packaging such as in bottles.

As indicated above, disintegrants are often included to ensure that the tablet has an acceptable rate of disintegration. Typical disintegrants include starch derivatives and salts of carboxymethylcellulose. Thus, there still exists a need for non-sticking tabletable compositions which, can be used to make fast-dissolving, pleasant tasting dosage forms at a low cost and without the need for excessive amounts of super disintegrant or complicated processing equipment.

SUMMARY OF THE INVENTION

The present invention is based on the unexpected discovery that quick dissolve Flashdose™ tablets can be provided without the need for floss matrices. The inventors have unexpectedly discovered that under certain processing conditions, direct compression of Liquiflash™ microspheres, in particular microspheres prepared according to co-owned U.S. patent application Ser. No. 09/179,926 (now abandoned) provides quick dissolve dosage without the need for a floss matrix or super disintegrant as defined below or with quantities of super disintegrant that are well below the levels employed with the dosage forms discussed in the background section.

In addition to the fast dissolve properties provided by the compositions of the invention, other advantages of the invention include the use of appropriate excipient mass (e.g., directly compressible inorganic salt; cellulose derivatives, etc.), which in turn facilitates the processing of the composition and eliminates the need for complex processing equipment. The components of the composition of the invention and the processing methods associated therewith allow for substantially lowering the cost associated with the production of the quick dissolve dosage forms of the invention which in turn facilitates their use at a large scale. Also, the simplicity of the excipients and the techniques employed in forming the dosage forms of the invention reduces the number of steps in manufacturing the dosage forms, thereby drastically reducing the opportunities for contamination and other quality impacting deleterious effects. The dosage forms of the invention are also advantageous in that higher loads of active agent can be obtained.

As well, the compositions and dosage forms of the invention are greatly advantageous in that packaging is simplified. In fact, the present invention provides a unique combination of materials and processing techniques that allows the packaging of quick dissolve dosage forms in recipients as commonly used and easy to access as prescription or over the counter bottles and blister packaging. The simpler packaging advantages of the composition of the invention are due at least in part to the improved friability and hardness obtained with the quick dissolve dosage forms of the invention.

In one embodiment, the invention provides a composition useful for making oral dosage forms capable of dissolving in the mouth in less than 40 seconds without the need for a conventional super disintegrant and having a friability of less than 1%; wherein the composition comprises drug-containing liquiflash particles and an excipient mass. Preferred excipient mass comprises a directly compressible inorganic salt, a cellulose derivative or a mixture of a directly compressible salt and a cellulose derivative. Preferably, the liquiflash particles and the mass of excipient are combined in proportions such that the active ingredient remains substantially within the microspheres when the composition is compressed to obtain a dosage form having a hardness of about 20 N to 50 N. The improved hardness and friability are obtained due to the discovery that the combination of the microspheres and the excipient mass allows for higher compression force.

The liquiflash particles are preferably coated with at least one taste-masking coating. The coating preferably contains at least one cellulosic polymer. To improve the dissolution properties of the dosage form of the invention the composition can further comprises microcrystalline cellulose which facilitates disintegration in the mouth without having super disintegrant properties. A preferred linear polyol comprises manitol, alone or in combination with sorbitol.

A preferred embodiment of the invention provides a composition useful for making oral dosage forms capable of dissolving in the mouth in less than 30 seconds and having a friability of less than 1%; wherein the composition comprises liquiflash particles containing at least one bioaffecting agent and a combination of at least one solubilizer and at least one spheronization aid, said liquiflash particles being coated after spheronization; a mass comprising an excipient mass and less than 2.5% by weight of a super disintegrant.

As indicated below, the compositions of the invention can be successfully employed to prepare oral dosage forms of a variety of active agents. Particularly preferred active agents include fluoxetine; paroxetine and zolpidem.

DETAILED DESCRIPTION OF THE INVENTION

The invention is concerned with bio-affecting microparticles produced from compositions containing a unique combination of ingredients. The composition, the microparticles, their production and comestible units containing them are disclosed.

Unless stated otherwise, all percentages recited herein are weight percentages, based on total composition weight.

I. Disintegrants and Super Disintegrants:

A disintegrant is an excipient which is added to a tablet or capsule blend to aid in the break up of the compacted mass when it is put into a fluid environment. This is especially important for immediate release products where rapid release of drug substance is required. A disintegrant can be added to a powder blend for direct compression or encapsulation. It can also be used with products that are wet granulated. In wet granulation formulations, the disintegrant is normally effective when incorporated into the granule (intragranularly). However, it may be more effective if added 50% intragranularly, and 50% extra-granularly (i.e., in the final dry mixture). While there are some tablet fillers (e.g., starch and microcrystalline cellulose) which aid in disintegration, there are more effective agents referred to as superdisintegrants. Some superdisintegrants and their properties are listed below.

| | |
|---|---|
| Crosscarmelose sodium | High swelling capacity, effective at low concentrations (0.5-2.0% but can be used up to 5.0%). |
| Crospovidone | Completely insoluble in water. Rapidly disperses and swells in water, but does not gel even after prolonged exposure. Greatest rate of swelling compared to other disintegrants. Greater surface area to |

-continued

| | | |
|---|---|---|
| | | volume ratio than other disintegrants. Recommended concentration: 1 to 3% |
| | | Available in micronized grades if needed to improve uniform dispersion in the powder blend. |
| Sodium Starch Glycolate | | Absorbs water rapidly, resulting in swelling which leads to rapid disintegration of tablets and granules. |
| | | Recommended concentration: |
| | | 1.0-4.0% but may need to use up to 6.0%. Gels on prolonged exposure to water. High concentrations may cause gelling and loss of disintegration. |

A super disintegrant according to the invention is a disintegrant that has a Eq. Moisture content at 25 C/90% RH of over 50%. A list of exemplary disintegrants, super disintegrants and other formulations with some disintegrant qualities are provided below:

Superdisintegrants and Disintegrants

| Brand name | Common name | Classification | Functional Category | Properties | Eq. Moisture content at 25C/90% RH | Typical uses |
|---|---|---|---|---|---|---|
| CL-Kollidon | Crospovidone | Polyvinyl-polypyrrolidone | Tablet super disintegrant | Hygroscopic Swelling-18% in 10 s, 45% in 20 s | 62% | Disintegrant in dry and wet granulation |
| Ac-Disol Primellose | Croscarmellose sodium | Cellulose, carboxymethyl ether, sodium salt, crosslinked | Tablet and capsule super disintegrant | Hygroscopic Wicking and swelling-12% in 10 s, 23% in 20 s | 88% | Disintegrant for capsules, tablets and granules |
| Explotab Primojel | Sodium starch glycolate | Sodium carboxymethyl starch | Tablet and capsule super disintegrant | Swelling capacity: in water swells up to 300 times its volume | | Disintegrant in dry and wet granulation |
| Explotab V17 | Sodium starch glycolate | (Cross linked low substituted carboxymethyl ether)Sodium carboxymethyl starch | Super disintegrant | Swells to greater extent than explotab | | Disintegration and dissolution aid. Not for use in wet granulation |
| Explotab CLV | Sodium starch glycolate | (Cross linked low substituted carboxymethyl ether)Sodium carboxymethyl starch, highly cross linked | Super disintegrant | | | Designed for wet granulation that utilize high shear equipment |
| L-HPC | Hydroxypropyl cellulose, low-substituted | Cellulose, 2-hydroxypropyl ether (low substituted) | Tablet and capsule disintegrant, tablet binder | Hygroscopic Swelling-13% in 10 s, 50% in 20 s | 37% | Tablet disintegrant, binder in wet granulation |
| Amberlite IRP 88 | Polacrilin Potassium | Cation exchange resin | Tablet disintegrant | Swelling ability | | Tablet disintegrant |
| Starch 1500 | Starch, pregelatinized | Pregelatinized starch | Tablet and capsule diluent, disintegrant, tablet binder | Hygroscopic | 22% | Capsule and tablet binder, diluent, disintegrant |

-continued

| Superdisintegrants and Disintegrants | | | | | | |
|---|---|---|---|---|---|---|
| Brand name | Common name | Classification | Functional Category | Properties | Eq. Moisture content at 25C/90% RH | Typical uses |
| Avicel | Microcrystalline cellulose | Cellulose | Tablet and capsule diluent, tablet disintegrant | Hygroscopic Swelling- 12% in 10 s, 18% in 20 s | 18% | Binder/diluent, has also some lubricant and disintegrant properties |

II. Compositions

The compositions of the invention employ optional excipients with (a) a bioaffecting agent and (b) one or more processing aids.

A. Bio-affecting Agents

The active ingredients useful herein can be selected from a large group of therapeutic agents. Respective classes include those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; antimigraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; anti-ulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others. Active agents which may be used in the invention include: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorhydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine and its hydrochloride; cinnamedrine hydrochloride; citalopram; citric acid; clarithromycin; clemastine and its flumarate; clonidine and its hydrochloride salt; clorfibrate; cocoa butter; cod liver oil; codeine and its fumarate and phosphate; cortisone acetate; ciprofloxacin HCI; cyanocobalamin; cyclizine hydrochloride; cyproheptadine and its hyddrochloride; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fluoxetine; folic acid; fosphenytoin; 5-fluorouracil (5-FU); fluoxetine and its hydrochloride; flurbiprofen; furosemide; gabapentan; gentamicin; gemfibrozil; glipizide; glycerine; glyceryl stearate; granisetron and its hydrochloride; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its monoand dinitrates; isoxicam; ketamine; kaolin; ketoprofen; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; meclizine and its hyddrochloride; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/ hydrates; metronidazole and its hydrochloride; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine and its hydrochloride salt; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCI; vidaribine phosphate; vitamins A, B, C, D, BI, B2, B6, B,2, E, and K; witch hazel; xylometazoline hydrochloride; zinc; zinc sulfate; zinc undecylenate. Mixtures and pharmaceutically acceptable salts of these and other actives can be used.

Particularly useful active agents are sparingly soluble solid agents whose dissolution and release properties are enhanced by the solubilizing agents used herein. These agents include HZ antagonists, analgesics, including non-steroidal anti-inflammatory drugs (NSAIDs), anticholesterolemics, anti-allergy agents, and anti-migraine agents.

Analgesics include aspirin, acetaminophen, acetaminophen plus caffeine, and non-steroidal anti-inflammatory drugs (NSAIDS), e.g., ibuprofen and nimesulide.

Useful NSAIDs include ibuprofen; diclofenac and its alkali metal salts; fenoprofen and its metal salts; fluriprofen; ketoprofen; naproxen and its alkali metal salts; nimesulide; and piroxicam and its salts.

$H_2$-antagonists which are contemplated for use in the present invention include cimetidine, ranitidine hydrochloride, famotidine, nizatidine, ebrotidine, mifentidine, roxatidine, pisatidine and aceroxatidine.

Useful anti-allergy agents include hydricodone and its tartrates; clemastine and its fumarate; azatadine and its maleate; acetaminophen; hydroxyzine and its pamoate and hydrochloride salts; chlorpheniramine and its maleates and tannates; pseudoephedrine and its sulfates and hydrochlorides; broinopheniramine and its maleate; dextromethorphan and its hydrohalides; loratadine; phenylephrine and its tannates and hydrochlorides; methscopolamine and its nitrates; phenylpropanolamine and its hydrochlorides; codeine and its hydrochloride; codeine and its phosphate; terfenadine; acrivastine; astemizole; cetrizine and its hydrochloride; phenindamine and its tartrate; tripelennamine and its hydrochloride; cyproheptadine and its hydrochloride; promethazine and its hydrochloride; and pyrilamine and its hydrochlorides and tannates.

Useful antimigraine agents include divalproex and its alkali metal salts; timolol and its maleate; propanolol and its hydrohalides; ergotamine and its tartrate; caffeine; sumatriptan and its succinate; dihydroergotamine, its hydrogenates/mesylates; methsergide and its maleate; isometheptene mucate; and dichloralphenazone.

Another class of drugs which can be used are antiemetics. Useful antiemetics include: meclizine and its hydrochloride; hydroxyzine and its hydrochloride and pamoate; diphenhydramine and its hydrochloride; prochlorperazine and its maleate; benzquinamide and its hydrochloride; granisetron and its hydrochloride; dronabinol; bismuth subsalicylate; promethazine and its hydrochloride; metoclopramide and its halides/hydrates; chlorpromazine; trimethobenzamide and its hydrochloride; thiethylperazine and its maleate; scopolamine; perphenazine; and ondansetron and its hydrochloride.

Other active ingredients for use in the present invention include antidiarrheals such as immodium AD, antihistamines, antitussives, decongestants, vitamins, and breath freshners. Also contemplated for use herein are anxiolytics such as Xanax; antipsychotics such as Clozaril and Haldon; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigranes such as Imigran, ACE-inhibitors such as Vasotec, Capoten and Zestril; Anti-Alzheimers agents such as Nicergoline; and Call-Antagonists such as Procardia, Adalat, and Calan.

Among the anticholesterolemics, the statins, e.g., lovastatin, provastatin and the like are notable.

Fluoxetine, paroxetine and zolpidem are preferred active agents.

Combinations of various types of drugs, as well as combinations of individual drugs, are contemplated.

B. Processing Aids

The processing aids of the invention include high molecular weight polyethylene glycols (PEG's) and/or polyethylene glycol glyceryl esters. When microspheres are made, these materials can be called "spheronization aids."

By "high molecular weight polyethylene glycols (PEG)," applicants mean PEG's having molecular weights of about 3,000 to about 8,000. "PEG 4600," having an average molecular weight of about 4400 to 4800, is a preferred material. Mixtures can be used.

In chemical terms, useful PEGs are those molecules having the structural formula $HOCH_2$ $(CH_2OCH^2)^m$ $CH_2OH$, wherein m is the average number of oxyethylene groups. PEG's used for this invention are those in which m is from about 0 to about 13.

Useful PEGS are solids. They are discussed on pages 355-361 of the *Handbook of Pharmaceutical Excipients*, $2^{nd}$ ed. (1994).

The polyethylene glycol glyceryl esters useful herein are selected from those containing about 30 to about 35 oxyethylene groups. Polyethylene glycol 32 glyceryl ester sold as "GELUCIRE 50/13" by Gattefosse S. A. of France is a preferred ester. Mixtures are operable.

The amounts of ingredients used in the compositions are generally within those shown in the following table.

|  | Broad range | Narrow range | Preferred range |
| --- | --- | --- | --- |
| Bio-affecting agent(s) | 1-50% | 5-40% | 20-30% |
| PEG | 0-90% | 60-90% | 60-80% |
| Glyceryl ester | 0-60% | 1-10% | 2.5-7.5% |
| Excipient(s) | 0-98% | 10-50% | 10-30% |

III. Processes

Useful processes for making the microparticles of the invention include liquiflash conditions as well as other thermoforming processes known in the art, eg., extrusion. "Liquiflash conditions" are generally those under which the material, called a feedstock, is rapidly heated just to the point at which it undergoes intraparticulate flow and partially deforms or liquifies so that it can pass through openings in a suitable spinning device. The passage of the liquiflash particles through openings is in response to centrifugal forces within the spinning head, which forces "expel" the particles, as discrete solids out of the device and into the atmosphere. The expelled materials instantly reform into particles, without the application of external shaping forces, which particles have different morphologies from those of the feedstocks.

Applicants have found that one particular spinning device is highly useful in making the microspheres of the invention. In U.S. Pat. No. 5,458,823, a spinning device is described which uses a spinning head including a base and a cover. A plurality of closely spaced heating elements are positioned between the base and cover, forming a barrier through which the material to be processed passes. In use, the head rotates and the heating elements are heated to temperatures that bring about liquiflash conditions in the materials being processed. As the spinning head rotates, the centrifugal force created by its rotation expels the material through spaces between the heating elements. The material forms discrete, generally spherical particles as it exits.

The production of microspheres for use in the subject invention may be optimized by the use of a V-groove insert inside the spinner head. The insert is described in U.S. Pat. No. 5,851,454, filed Jun. 13, 1997 The insert has grooves therein, which grooves have a uniform depth and width through their length, so that highly uniform discrete microspheres or other particles are produced. Using this or a similar insert, the spinning device is operated at 50 to 75 Hz, at about 10 to 25% power, and at temperatures which yield liquiflash conditions.

It should be noted that "liquiflash conditions" vary with the properties of the material, or feedstock, being processed. Since the feedstocks contain many substances in varying amounts, the parameters need to yield "liquiflash conditions" for a particular mixture must be ascertained by processing small quantities or samples before processing large ones. Typically, the feedstocks contain active agent(s) and processing aids.

Among the co-assigned patents and patent applications which describe the preparations of microspheres containing bio-affecting agents re: U.S. Pat. No. 5,458,823; U.S. Pat. No. 5,683,720; and U.S. Pat. No. 5,851,454.

III. Microparticles

While particulates made using various thermoprocessing technologies are useful, microspheres described below are preferred.

The microspheres or other particulates are generally solid spherical bodies of about 150 to about 250 microns mean particle diameter.

It is preferred that they be produced via a direct spheronization process, such as liquiflash or other suitable techniques. However, they may be made by physically altering the size and/or shape of non-spherical particles by extrusion/spheronization or melt granulation processes.

When microspheres are made by direct spheronization of compositions containing active agent(s), the fatty esters and optional emulsifiers/surfactants, the fatty esters function as spheronization aids.

The microspheres may be used as is, i.e., in powder or sachet products for delivering active agents. Alternatively, they may be used in the production of solid, liquid (suspensions), or semi-solid (e.g., gel-like) comestible units, etc. Tablets and capsules are preferred.

It is preferred that the microspheres of the invention be used in combination with an excipient mass, without a floss matrix.

Once the excipient mass and microsphere ingredients are combined, they can be shaped into comestible units.

IV. Coatings

One or both of the microspheres and the dosage units can be coated or encapsulated with at least one coating. Useful coating formulations contain polymeric ingredients as well as excipients conventionally employed in such coatings. The coatings are generally used for such purposes as taste-masking, controlling release and the like.

Useful taste-masking coatings can include (meth)acrylate/cellulosic polymers. Ethylcellulose (EC), hydroxypropylcellulose (HPC), hydroxypropylmethylcellulose (HPMC), and polymethacrylate polymers, such as Eudragit RS, Eudragit RL or mixtures thereof are useful. Preferred combinations include EC/HPC and Eudragit RS/Eudragit RL.

Controlled release coatings generally contain at least one of: ethylcellulose (EC), hydroxypropylcellulose (HPC), hydroxypropylmethyl cellulose (HPMC), hydroxypropylmethylcellulose phthalate, cellulose acetate phthalate, and the like. The "Eudragits" designated as NE 300, RS, L 30 D, are useful. Mixtures are operable.

Coating levels of about 0 to about 150% are effective, with levels of about 5% to about 30% being preferred.

Coating devices include those conventionally used in pharmaceutical processing, with fluidized bed coating devices being preferred.

Formulations according to the invention are illustrated by the examples provided below, which should in no way limit the scope of the appended claims. The friability results shown below correspond to Drop tests conducted with a Roche drum equiped with two seperatedrums, the motor rotate the drum at 100 revolution/min. the actual drums is made from plexiglass and is seperated into parts, the drum body and removable cover, which opens to fill, discharge and clean the drum. For the Abrasion tests one of the two drums is replaced with an abrasion drum.

EXAMPLES

The examples and counterexamples provided below illustrate formulations and processing conditions for forming dosage forms according to the invention.

Formulatin No 1

CEFORM™ or other coated particle: 5-45% W/W, preferred 5-35%, (35-45% is fast tablet but gritty)

Mannitol*: 29.1-77.1%

Microcrystalline Cellulose**: 12-18% l-HPC, LH-11: 2-4%

Citric Acid: 1.5%

Acesulfame K: 0.2%

Magnasweet 100: 0.2%

Flavor: 0.5%

Syloid: 0.5%

Pruv: 1.0%

Formulation NO 2

CEFORM™ or other coated particle: 5-45% W/W, preferred 5-35%, (35-45% is fast tablet but gritty)

Mannitol*: 29.1-77.1%

Microcrystalline Cellulose**: 12-18%, preferably 15%-18%

Kollidon CL: 2-4%

Citric Acid: 1.5%

Acesulfame K: 0.2%

Magnasweet 100: 0.2%

Flavor: 0.5%

Syloid: 0.5%

Pruv: 1.0%

Formulation No 3 (more referred platform):

CEFORM™ or other coated particle: 5-45% W/W, preferred 5-35%, (35-45% is fast tablet but gritty)

Mannitol*: 27.1-83.6%

Microcrystalline Cellulose**: 5-20%, preferably 15-18%

Kollidon CL: 2%

1-HPC, LH-11: 2%

Citric Acid: 1.5%

Acesulfame K: 0.2%

Magnasweet 100: 0.2%

Flavor: 0.5%

Syloid: 0.5%

Pruv: 1.0%

*Mannitols evaluated and found acceptable: Pearlitol 400DC, 300DC, Parteck M200, Parteck M300, Roquette Lab 3038. No differences were observed in disintegration time.
**Microcrystalline cellulose evaluated and found acceptable: Avicel PH 101, 102, 113, Prosolv 50, Prosolv 90. No differences were observed in disintegration time.

Other preferred formulations based on model drug fluoxetine:

| Formulation Lot# | Hardness (N) | Disintegration time | Friability % | Comments |
|---|---|---|---|---|
| FluoxetineTMMS: 28.69<br>Pearlitol 400DC: 48.41<br>Avicel PH 101: 16.0<br>L-HPC 11: 4.0<br>Citric acid: 1.0<br>AsesulK: 0.2<br>Tangerine: 0.2<br>Syloid: 0.5<br>Pruv: 1.0<br>Avicel PH101/L-HPC11 ratio (80/20)<br>Lot#/mfg date: 1242-124<br>250 g batch/11 mm<br>Flat Face Radial Edge/450 mg | 29.7 | Mouth: 10 s<br>USP basket rack assembly: 20 s | 0.8 | Can be used with any drug |
| FluoxetineTMMS: 28.69<br>Pearlitol 400DC: 48.41<br>Avicel PH 101: 18.0<br>L-HPC 11: 2.0<br>Citric acid: 1.0<br>AsesulK: 0.2<br>Tangerine: 0.2<br>Syloid: 0.5<br>Pruv: 1.0<br>Avicel PH101/L-HPC11 (90/10) ratio<br>Lot#/mfg date: 1242-125<br>250 g batch/11 mm<br>Flat Face Radial Edge/450 mg | 34.0 | Mouth: 10 s<br>USP basket rack assembly: 20 s | 0.8 | Can be used with any drug |
| FluoxetineTMMS: 28.69<br>Pearlitol 400DC: 51.41<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0<br>*can be | 29.5<br>24.4<br>28.4<br>26.0<br>28.3 | Mouth: 10 s,<br>15 s, 20 s, 10 s,<br>10 s<br>USP basket rack assembly:<br>15 s, 20 s, —,<br>19 s, — | 0.3<br>0.3<br>0.2<br>0.2<br>0.4 | Can be used with any drug |

-continued

| | | | | |
|---|---|---|---|---|
| Avicel 113, 1242-140<br>Avicel 102, 1242-139<br>Prosolv 50, 1242-138<br>Prosolv 90, 1242-137<br>Lot#/mfg date: 1242-<br>135, 140, 139, 138,<br>137<br>250 g batch/11 mm<br>Flat Face Radial<br>Edge/450 mg | | | | |
| FluoxetineTMMS:<br>28.69<br>Advantose 100:<br>12.85<br>Pearlitol 400DC:<br>38.56<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0<br>Advantose<br>100/Pearlitol 400DC<br>(25/75) ratio<br>Lot#/mfg date: 1242-<br>148/<br>Feb. 4, 2002<br>250 g batch/11 mm<br>Flat Face Radial<br>Edge/450 mg | 28.4 | Mouth: 15 s.<br>Good tablets<br>No significant<br>difference<br>between 1242-<br>147<br>USP basket<br>rack assembly:<br>19 s | 0.5 | Can be used with any drug except the drugs that have amine group. |
| FluoxetineTMMS:<br>28.69<br>Pearlitol 400DC:<br>51.41<br>Avicel PH 101: 15.0<br>Kollidon CL: 2.0<br>Citric acid: 1.0<br>AsesulK: 0.2<br>Syloid: 0.5<br>Tangerine: 0.2<br>Pruv: 1.0<br>Lot#/mfg date: 1242-<br>152/<br>Feb. 5, 2002<br>250 g batch/11 mm Flat<br>Face Radial<br>Edge/450 mg | 33.9 | Mouth: 7-10 s<br>very fast tablet<br>USP basket<br>rack assembly:<br>31 s | 0.6 | Can be used with<br>any drug |
| FluoxetineTMMS:<br>28.69<br>Pearlitol 400DC:<br>38.56<br>Advantose 100: 12.85<br>Avicel PH 101: 15.0<br>Kollidon CL: 2.0<br>Citric acid: 1.0<br>AsesulK: 0.2<br>Syloid: 0.5<br>Tangerine: 0.2<br>Pruv: 1.0<br>Lot#/mfg date: 1242-<br>153/<br>Feb. 5, 2002<br>250 g batch/11 mm Flat<br>Face Radial<br>Edge/450 mg | 30.8 | Mouth: 10 s<br>very fast tablet<br>USP basket<br>rack assembly:<br>19 s | 0.2 | Can be used with<br>any drug except the<br>drugs that have<br>amine group. |
| FluoxetineTMMS:<br>28.69<br>Pearlitol 400DC:<br>49.41<br>Avicel PH 101: 15.0<br>Kollidon CL: 2.0<br>L-HPC 11: 4.0<br>Citric acid: 1.0<br>AsesulK: 0.2<br>Syloid: 0.5 | 29.4 | Mouth: 10 s<br>very fast tablet,<br>no difference<br>between 1242-<br>154 & 140<br>batches<br>USP basket<br>rack assembly:<br>23 s | 0.6 | Can be used with<br>any drug |

-continued

| | | | | |
|---|---|---|---|---|
| Tangerine: 0.2<br>Pruv: 1.0<br>Lot#/mfg date: 1242-157/<br>Feb. 6, 2002<br>250 g batch/11 mm Flat Face Radial Edge/450 mg<br>FluoxetineTMMS: 28.69<br>Pearlitol 400DC: 37.06<br>Advantose 100: 12.35<br>Avicel PH 101: 15.0<br>Kollidon CL: 2.0<br>L-HPC 11: 2.0<br>Citric acid: 1.0<br>AsesulK: 0.2<br>Syloid: 0.5<br>Tangerine: 0.2<br>Pruv: 1.0<br>Lot#/mfg date: 1242-158/<br>Feb. 6, 2002<br>250 g batch/11 mm Flat Face Radial Edge/450 mg | 33.1 | Mouth: 12-15 s<br>good tablet<br>USP basket<br>rack assembly:<br>12 s | 0.6 | Can be used with any drug except the drugs that have amine group. |

| | | | | |
|---|---|---|---|---|
| Fast Disintegrating Non Floss Tablet Additional Preferred Formulation | | | | |
| FluoxetineTMMS: 28.69<br>Pearlitol 400DC: 48.41<br>Avicel PH 101: 16.0<br>Kollidon CL: 2.0<br>L-HPC 11: 2.0<br>Citric acid: 1.0<br>AsesulK: 0.2<br>Magnasweet 100: 0.2<br>Tangerine: 0.2<br>Syloid: 0.5<br>Pruv: 1.0<br>Lot#/mfg date: 1242-167/<br>Feb. 13, 2002<br>250 g batch/11 mm Flat Face Radial Edge/450 mg | 28.4 | Mouth: 8-10 s<br>very good<br>tablet<br>USP basket<br>rack assembly<br>12 s | 0.5 | Can be used with any drug |

Additional formulations:

| Formulation Lot# | Objective | Mixing procedure & Equipment used | Hardness (N) | Disintegration Time | Friability % |
|---|---|---|---|---|---|
| Fluoxetine TMMS: 28.69<br>Pearlitol 400DC: 58.41<br>Kolidon XL: 10<br>Citric acid: 1.0<br>AsesulK: 0.2<br>Tangerine: 0.2<br>Syloid: 0.5<br>Pruv: 1.0<br>Lot#/mfg date:<br>1242-117/Jan. 14, 2002<br>250 g batch | Investigate high level of Kollidon XL for fast disintegration using high compression. | ½ Pearlitol 400DC, all MS<br>½ Pearlitol 400DC, mix for 3 min. Add all Citric acid, all AcesuK, all syloid, all Kollidon, all tangerine, mix for 5 min. Then pour all pruv and mix for 2 min using Turbula mixer.<br>Piccola tablets press 11 mm punch FFRE 450 mg table | 32.4 | Mouth: 10 S | Abrasion: 0.3<br>Drop: 2.1 |
| Fluoxetine TMMS: 28.69<br>Pearlitol 400DC: 58.41<br>Kolidon XL: 10<br>Citric acid: 1.0<br>AsesulK: 0.2<br>Tangerine: 0.2 | Evaluate different from different suppliers. | ½ Parteck M200, all MS,<br>½ Parteck M200 mix for 3 min. Add all Citric acid, all AcesuK, all syloid, all Kollidon, all tangerine, mix for 5 | 22.2 | Mouth: 10 S | Abrasion: 1.4<br>Drop: 4.1 |

-continued

| Composition | Purpose | Procedure | | | |
|---|---|---|---|---|---|
| Syloid: 0.5<br>Pruv: 1.0<br>Lot#/mfg date:<br>1242-118/Jan. 14, 2002<br>250 g batch | | min. Then pour all pruv and mix for 2 min. using Turbula mixer.<br>Piccola tablets press<br>11 mm punch FFRE<br>450 mg tablet | | | |
| Fluoxetine TMMS:<br>28.69<br>Pearlitol 400DC:<br>58.41<br>Kolidon XL: 10<br>Citric acid: 1.0<br>AsesulK: 0.2<br>Tangerine: 0.2<br>Syloid: 0.5<br>Pruv: 1.0<br>Lot#/mfg date:<br>1242-119/Jan. 14, 2002<br>250 g batch | Evaluate different mannitol from different suppliers. | ½ Parteck M300, all MS<br>½ Parteck M300, mix for 3 min. Add all Citric acid, all AcesuK, all syloid, all Kollidon, all tangerine, mix for 5 min. Then pour all pruv and mix for 2 min. using Turbula mixer.<br>Piccola tablets press<br>11 mm punch FFRE<br>450 mg tablet | 29.9 | Mouth: 10 S | Abrasion<br>0.8<br>Drop:<br>3.0 |
| Fluoxetine TMMS:<br>28.69<br>Pearlitol 400DC:<br>48.41<br>Kolidon XL: 20<br>Citric acid: 1.0<br>AsesulK: 0.2<br>Tangerine: 0.2<br>Syloid: 0.5<br>Pruv: 1.0<br>Lot#/mfg date:<br>1242-120/Jan. 15, 2002<br>250 g batch | Increase the Kollidon XL from 10% to 20% to determine the effect of disintegrant concentration on disintegration time | ½ Pearlitol 400DC, all MS<br>½ pearlitol 400DC, mix for 3 min. Add all Citric acid, all AcesuK, all syloid, all Kollidon, all tangerine, mix for 5 min. Then pour all pruv and mix for 2 min using Turbula mixer.<br>Piccola tablets press<br>11 mm punch FFRE | 29.6 | Mouth: 10 S | Abrasion<br>0.4<br>Drop:<br>2.3 |
| Fluoxetine TMMS:<br>28.69<br>Pearlitol 400DC:<br>48.41<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date:<br>1242-123/Jan. 16, 2002<br>250 g batch | Investigate alternative distintegrant like L-HPC11 | ½ Pearlitol 400DC, all MS<br>½ Pearlitol 400DC, mix for 3 min. Add all Citric acid, all AcesuK, all syloid, all L-HPC, all tangerine, mix for 5 min. Then pour all pruv and mix for 2 min using Turbula mixer.<br>Piccola tablets press<br>11 mm punch FFRE<br>450 mg tablet | 16.2 | Mouth: 20 S at 20 and 30 N tablets<br>Verty slow to disintegrate | Abrasion<br>14.8<br>Drop:<br>Powder collection |
| Fluoxetine TMMS:<br>28.69<br>Pearlitol 400DC:<br>48.41<br>Avicel PH 101: 16.0<br>L-HPC 11: 4.0<br>Citric acid: 1.0<br>AsesulK: 0.2<br>Tangerine: 0.2<br>Syloid: 0.5<br>Pruv: 1.0<br>Lot#/mfg date:<br>1242-124/Jan. 16, 2002<br>250 g batch<br>Avicel PH101/L-HPC11 ratio<br>(80/20) | Increase the Kollidon XL from 10% to 20% to determine the effect of disintegrant concentration on disintegration time | ½ Pearlitol 400DC, all MS<br>½ pearlitol 400DC, mix for 3 min. Add all Citric acid, all AcesuK, all syloid, all avicel, all L-HPC, all tangerine, mix for 5 min. Then pour all pruv and mix for 2 min using Turbula mixer.<br>Piccola tablets press<br>11 mm punch FFRE<br>450 mg tablet | 29.7 | Mouth: 10 S | Abrasion<br>0.2<br>Drop:<br>0.8 |
| Fluoxetine TMMS:<br>28.69<br>Pearlitol 400DC:<br>48.41<br>Avicel PH 101: 18.0<br>L-HPC 11: 2.0<br>Citric acid: 1.0<br>AsesulK: 0.2<br>Tangerine: 0.2 | Evaluate different ratio of avicel PH 101/L-HPC 11 to determine which excipient | ½ Pearl 400DC, all MS<br>½ Pearlitol 400DC, mix for 3 min. Add all Citric acid, all AcesuK, all syloid, all avicel, all L0HPC, all tangerine, mix for 5 min. Then pour all | 34.0 | Mouth: 10 S | Abrasion<br>0.2<br>Drop:<br>0.8 |

-continued

| | | | | | |
|---|---|---|---|---|---|
| Syloid: 0.5<br>Pruv: 1.0<br>Lot#/mfg date:<br>1242-125/Jan. 16, 2002<br>250 g batch<br>Avicel PH 101/L-<br>HPC11 ratio<br>(90/10) | affect more<br>the<br>disintegration<br>in the<br>mouth. | pruv and mix for 2<br>min using Turbula<br>mixer.<br>Piccola tablets press<br>11 mm punch FFRE<br>450 mg table | | | |
| Fluoxetine TMMS:<br>28.69<br>Pearlitol 400DC:<br>48.41<br>Avicel PH 101: 18.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date:<br>1242-129/Jan. 19, 2002<br>250 g batch<br>Avicel PH 101/L-<br>HPC11 ratio<br>(90/10) | Evaluate<br>different<br>ratio of<br>avicel PH<br>101/L-HPC<br>11 to<br>determine<br>which<br>excipient<br>affect more<br>the<br>disintegration<br>in the<br>mouth. | ½ Pearlitol 400DC,<br>all MS,<br>½ Pearlitol 400DC,<br>mix for 3 min. Add<br>all Citric acid, all<br>AcesuK, all syloid,<br>all Kollidon, all<br>tangerine, mix for 5<br>min. Then pour all<br>pruv and mix for 2<br>min. using Turbula<br>mixer.<br>Piccola tablets press<br>11 mm punch FFRE<br>450 mg tablet | 31.0 | Mouth: 10 S | Abrasion<br>0.2<br>Drop:<br>1.0 |
| Fluoxetine TMMS:<br>28.69<br>Pearlitol 400DC:<br>48.41<br>Avicel PH 101: 16.0<br>Kollidon XL: 4.0<br>Citric acid: 1.0<br>AsesulK: 0.2<br>Tangerine: 0.2<br>Syloid: 0.5<br>Pruv: 1.0<br>Lot#/mfg date:<br>1242-126/Jan. 17, 2002<br>250 g batch<br>Avicel PH<br>101/Kollidon ratio<br>(80/20) | Comparative<br>study of<br>disintegration<br>time of<br>avicel PH<br>101/L-<br>HPC11<br>formulation<br>versus<br>avicel PH<br>101/Kollid<br>on XL | ½ Pearlitol 400DC,<br>all MS,<br>½ Pearlitol 400DC,<br>mix for 3 min. Add<br>all Citric acid, all<br>Acesu K, all syloid,<br>all avicel, all<br>Kollidon, all<br>tangerine, mix for 5<br>min. Then pour all<br>pruv and mix for 2<br>min using Turbula<br>mixer.<br>Piccola tablets press<br>11 mm punch FFRE<br>450 mg tablet | 33.8 | Mouth 10:<br>10 S | Abrasion<br>0.1<br>Drop:<br>1.5 |
| Fluoxetine TMMS:<br>28.69<br>Pearlitol 400DC:<br>48.41<br>Avicel PH 101: 4.0<br>Kollidon XL: 16.0<br>Citric acid: 1.0<br>AsesulK: 0.2<br>Tangerine: 0.2<br>Syloid: 0.5<br>Pruv: 1.0<br>Lot#/mfg date:<br>1242-127/Jan. 17, 2002<br>250 g batch<br>Avicel PH<br>101/Kollidon ratio<br>(20/80) | Comparative<br>study of<br>disintegration<br>time of<br>avicel PH<br>101/L-<br>HPC11<br>formulation<br>versus<br>avicel PH<br>101/Kollid<br>on XL | ½ Pearlitol 400DC,<br>all MS,<br>½ Pearlitol 400DC,<br>mix for 3 min. Add<br>all Citric acid, all<br>Acesu K, all syloid,<br>all avicel, all<br>Kollidon, all<br>tangerine, mix for 5<br>min. Then pour all<br>pruv and mix for 2<br>min using Turbula<br>mixer.<br>Piccola tablets press<br>11 mm Punch FFRE<br>450 mg tablet | 31-37 | Mouth 10:<br>10 S | Abrasion<br>0.04<br>Drop:<br>1.6 |
| Fluoxetine TMMS:<br>28.69<br>Pearlitol 400DC:<br>52.41<br>Kollidon XL: 16.0<br>Citric acid: 1.0<br>AsesulK: 0.2<br>Tangerine: 0.2<br>Syloid: 0.5<br>Pruv: 1.0<br>Lot#/mfg date:<br>1242-130/Jan. 19, 2002<br>250 g batch | Comparative<br>study of<br>disintegration<br>time of<br>16%<br>Kollidon to<br>10 and<br>20% | ½ Pearlitol 400DC,<br>all MS,<br>½ Pearlitol 400DC,<br>mix for 3 min. Add<br>all Citric acid, all<br>Acesu K, all syloid,<br>all avicel, all<br>Kollidon, all<br>tangerine, mix for 5<br>min. Then pour all<br>pruv and mix for 2<br>min using Turbula<br>mixer.<br>Piccola tablets press<br>11 mm punch FFRE<br>450 mg tablet | 36.4 | Mouth 10:<br>10 S | Abrasion<br>1.0<br>Drop:<br>2.5 |

| | | | | | |
|---|---|---|---|---|---|
| Fluoxetine TMMS: 28.69<br>Pearlitol 400DC: 26.25<br>Avicel PH 101: 26.25<br>L-HPC: 16<br>Citric acid: 1.0<br>AsesulK: 0.2<br>Tangerine: 0.2<br>Syloid: 0.5<br>Pruv: 1.0<br>Lot#/mfg date: 1242-131/Jan. 21, 2002<br>250 g batch | Increase the level of avicel to improve the disintegration time. Avicel is porous and therefore, it absorbs lot of water which helps the swelling of L-HPC | ½ Pearlitol 400DC, all MS,<br>½ Pearlitol 400DC, mix for 3 min. Add all Citric acid, all Acesu K, all syloid, all avicel, all L-HPC, all tangerine, mix for 5 min. Then pour all pruv and mix for 2 min using Turbula mixer.<br>F tablets press 11 mm punch FFRE. 450 mg tablet | 29.4 | Mouth: 10 s | Abrasion 1.7<br>Drop: 1.8 |
| Fluoxetine TMMS: 28.69<br>Pearlitol 400DC: 26.25<br>Avicel PH 101: 26.25<br>Kolidon XL: 16<br>Citric acid: 1.0<br>AsesulK: 0.2<br>Tangerine: 0.2<br>Syloid: 0.5<br>Pruv: 1.0<br>Lot#/mfg date: 1242-132/Jan. 21, 2002<br>250 g batch | Same objective as 1242-131, except Kollidon was used. | ½ Pearlitol 400DC, all MS<br>½ Pearlitol 400DC, mix for 3 min. Add all Citric acid, all AcesuK, all syloid, all Kollidon, all tangerine, mix for 5 min. Then pour all pruv and mix for 2 min using Turbula mixer.<br>F tablets press 11 mm punch FFRE 450 mg table | 29.7 | Mouth: 10 S | Abrasion 0.3<br>Drop: 1.8 |
| Ireland Formulation | Enalapril FD tablets 36 mg | | 26 | Mouth: 10 S | Abrasion 2.5<br>Drop: 0.3 |
| Fluoxetine TMMS: 28.69<br>Pearlitol 400DC: 54.41<br>Avicel PH 101: 12.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-133/Jan. 23, 2002<br>250 g batch | Investigate the effect of MCC on the disintegration of the tablets, Decrease MCC from 18 to 12% | ½ Pearlitol 400DC, all MS<br>½ Pearlitol 400DC, mix for 3 min. Add all Citric acid, all AcesuK, all syloid, all avicel, all L-HPCn, all tangerine, mix for 5 min. Then pour all pruv and mix for 2 min using Turbula mixer.<br>F tablets press 11 mm punch FFRE 450 mg table | 28.3 | Mouth: 15-20 S<br>Slower than 1242-125 | Abrasion 0.3<br>Drop 0.3 |
| Fluoxetine TMMS: 28.69<br>Pearlitol 400DC: 60.41<br>Avicel PH 101: 6.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-134/Jan. 23, 2002<br>250 g batch | Investigate the effect of MCC on the disintegration of the tablets. Decrease MCC from 18 to 6% | ½ Pearlitol 400DC, all MS<br>½ Pearlitol 400DC, mix for 3 min. Add all Citric acid, all AcesuK, all syloid, all avicel, all L-HPC, all tangerine, mix for 5 min. Then pour all pruv and mix for 2 min using Turbula mixer.<br>F tablets press 11 mm punch FFRE 450 mg table | 28.1 | Mouth: 20 S<br>Slower than 1242-133 | Abrasion 0.4<br>Drop 0.4 |
| Fluoxetine TMMS: 28.69<br>Pearlitol 400DC: 51.41<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0 | Decreasing the level of MCC from 18 to 12% in the formulation slowed down slightly the disintegration of the | ½ Pearlitol 400DC, all MS<br>½ Pearlitol 400DC, mix for 3 min. Add all Citric acid, all AcesuK, all syloid, all avicel, all L-HPC, all tangerine, mix for 5 min. Then pour all pruv and mix for 2 min using Turbula | 29.5 | Mouth: 10 S<br>As good as 1242-125 | Abrasion 0.3<br>Drop 0.3 |

-continued

| | | | | | |
|---|---|---|---|---|---|
| Lot#/mfg date: 1242-135/Jan. 24, 2002 250 g batch | tablets, but it appeared to be an optimum level in between. The level of MCC was decreased to 15% instead. | mixer. F tablets press 11 mm punch FFRE 450 mg table | | | |
| Fluoxetine TMMS: 28.69 Pearlitol 400DC: 53.41 Avicel PH 101: 15.0 Citric acid: 1.0 AsesulK: 0.2 Tangerine: 0.2 Syloid: 0.5 Pruv: 1.0 Lot#/mfg date: 1242-136/Jan. 24, 2002 250 g batch | To investigate if the use of L-HPC is necessary in the formulation to enhance the disintegration of the tablet. | ½ Pearlitol 400DC, all MS ½ Pearlitol 400DC, mix for 3 min. Add all Citric acid, all AcesuK, all syloid, all avicel, all tangerine, mix for 5 min. Then pour all pruv and mix for 2 min using Turbula mixer. F tablets press 11 mm punch FFRE 450 mg table | 27.5 | Mouth: 20 S Disintegrate with a core | Abrasion 0.2 Drop 0.4 |
| Fluoxetine TMMS: 28.69 Pearlitol 400DC: 51.41 Prosolv 90: 15.0 L-HPC 11:2.0 Citric acid: 1.0 AsesulK: 0.2 Tangerine: 0.2 Syloid: 0.5 Pruv: 1.0 Lot#/mfg date: 1242-137/Jan. 24, 2002 250 g batch | Investigate other grades of MCC | ½ Pearlitol 400DC, all MS ½ Pearlitol 400DC, mix for 3 min. Add all Citric acid, all AcesuK, all syloid, all prosolv, all tangerine, mix for 5 min. Then pour all pruv and mix for 2 min using Turbula mixer. F tablets press 11 mm punch FFRE 450 mg table | 28.3 | Mouth: 20 S As good as 1242-125 | Abrasion 0.2 Drop 0.4 |
| Fluoxetine TMMS: 28.69 Pearlitol 400DC: 51.41 Prosolv 90: 15.0 L-HPC 11: 2.0 Citric acid: 1.0 AsesulK: 0.2 Tangerine: 0.2 Syloid: 0.5 Pruv: 1.0 Lot#/mfg date: 1242-138/Jan. 24, 2002 250 g batch | Investigate other grades of MCC | ½ Pearlitol 400DC, all MS ½ Pearlitol 400DC, mix for 3 min. Add all Citric acid, all AcesuK, all syloid, all prosolv, all L-HPC, all tangerine, mix for 5 min. Then pour all pruv and mix for 2 min using Turbula mixer. F tablets press 11 mm punch EFRE 450 mg table | 26.0 | Mouth: 10 S Better than 1242-124 | Abrasion 0.3 Drop 0.2 |
| Fluoxetine TMMS: 28.69 Pearlitol 400DC: 51.41 Avicel PH 102": 15.0 L-HPC 11: 2.0 Citric acid: 1.0 AsesulK: 0.2 Tangerine: 0.2 Syloid: 0.5 Pruv: 1.0 Lot#/mfg date: 1242-139/Jan. 24, 2002 250 g batch | Investigate other greades of MCC | ½ Pearlitol 400DC, all MS ½ Pearlitol 400DC, mix for 3 min. Add all Citric acid, all AcesuK, all syloid, all avicel, all L-HPC, all tangerine, mix for 5 min. Then pour all pruv and mix for 2 min using Turbula mixer. F tablets press 11 mm punch FFRE 450 mg table | 28.4 | Mouth: 15S — 20 S | Abrasion 0.2 Drop 0.2 |
| Fluoxetine TMMS: 28.69 Pearlitol 400DC: 53.41 Avicel PH 113: 15.0 L-HPC 11: 2.0 Citric acid: 1.0 | Investigate other grades of MCC | ½ Pearlitol 400DC, all MS ½ Pearlitol 400DC, mix for 3 min. Add all Citric acid, all AcesuK, all syloid, all avicel, all L-HPC, | 24.4 | Mouth: 15 S | Abrasion 0.3 Drop: 0.3 |

-continued

| | | | | | |
|---|---|---|---|---|---|
| AsesulK: 0.2<br>Tangerine: 0.2<br>Syloid: 0.5<br>Pruv: 1.0<br>Lot#/mfg date:<br>1242-140/Jan. 25, 2002<br>250 g batch | | all tangerine, mix for 5 min. Then pour all pruv and mix for 2 min using Turbula mixer.<br>F tablets press 11 mm punch FFRE 450 mg table | | | |
| Fluoxetine TMMS: 28.69<br>Advantose 100: 68.41<br>Citric acid: 1.0<br>AsesulK: 0.2<br>Tangerine: 0.2<br>Syloid: 0.5<br>Pruv: 1.0<br>Lot#/mfg date:<br>1242-141/Jan. 25, 2002<br>250 g batch | To investigate alternative polyols. In this experiment, determine the compressibility of maltose (advantose 100) | ½ advantose, all MS ½ advantose, mix for 3 min. Add all Citric acid, all AcesuK, all syloid, all tangerine, mix for 5 min. Then pour all pruv and mix for 2 min using Turbula mixer.<br>F tablets press 11 mm punch FFRE 450 mg table | 26.9 | Mouth: 20 S with a core. Tablet sweet and have good mouthfeel. | Abrasion 0.8<br>Drop: 2.0 |
| Fluoxetine TMMS: 28.69<br>Advantose 100: 53.41<br>Prosolv 50: 15<br>Citric acid: 1.0<br>AsesulK: 0.2<br>Tangerine: 0.2<br>Syloid: 0.5<br>Pruv: 1.0<br>Lot#/mfg date:<br>1242-142/Jan. 27, 2002<br>250 g batch | To investigate alternative polyols. In this experiment, determine the compressibility of maltose (advantose 100) and MCC | ½ advantose, all MS ½ advantose, mix for 3 min. Add all Citric acid, all AcesuK, all syloid, all Prosolv, all tangerine, mix for 5 min. Then pour all pruv and mix for 2 min using Turbula mixer.<br>F tablets press 11 mm punch FFRE 450 mg table | 27.9 | Mouth: 10 S Not as good as 1242-143 | Abrasion 1.0<br>Drop: 4.2 |
| Fluoxetine TMMS: 28.69<br>Advantose 100: 51.41<br>Prosolv 50: 15<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date:<br>1242-143/Jan. 27, 2002<br>250 g batch | To investigate alternative poyols. In this experiment, determine the compressibility of maltose (advantose 100)/ MCC/L-HPC | ½ advantose, all MS ½ advantose, mix for 3 min. Add all Citric acid, all AcesuK, all syloid, all Prosolv, all tangerine, mix for 5 min. Then pour all pruv and mix for 2 min using Turbula mixer.<br>F tablets press 11 mm punch FFRE 450 mg table | 27.9 | Mouth: 10 S Good tablets | Abrasion 1.0<br>Drop: 3.7 |
| Fluoxetine TMMS: 28.69<br>Advantose 100: 61.41<br>Prosolv 50: 5<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date:<br>1242-144/Jan. 27, 2002<br>250 g batch | To investigate the effect of MCC on the disintegration of the tablets | ½ advantose, all MS ½ advantose, mix for 3 min. Add all Citric acid, all AcesuK, all syloid, all Prosolv, all L-HPC, all tangerine, mix for 5 min. Then pour all pruv and mix for 2 min using Turbula mixer.<br>F tablets press 11 mm punch FFRE 450 mg table | 26.3 | Mouth: 15 S Not as good as 1242-143. | Abrasion 0.6<br>Drop: 1.8 |
| Fluoxetine TMMS: 28.69<br>Advantose 100: 56.41<br>Prosolv 50: 10.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date:<br>1242-145/Jan. 27, 2002<br>250 g batch | To investigate the effect of MCC on the disintegration of the tablets | ½ advantose, all MS ½ advantose, mix for 3 min. Add all Citric acid, all AcesuK, all syloid, all Prosolv, all L-HPC, all tangerine, mix for 5 min. Then pour all pruv and mix for 2 min using Turbula mixer.<br>F tablets press 11 mm punch FFRE 450 mg table | | Mouth: 10-25 S Not as good as 1242-143. | Abrasion 0.0<br>Drop: 1.0 |

-continued

| | | | | | |
|---|---|---|---|---|---|
| Fluoxetine TMMS: 28.69<br>Advantose 100: 51.41<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-146/Feb. 4, 2002<br>250 g batch | To compare the use of avicel to prosolv and their effect on friability | ½ advantose, all MS ½ advantose, mix for 3 min. Add all Citric acid, all AcesuK, all syloid, all syloid, all avicel, all tangerine, mix for 5 min. Then pour all pruv and mix for 2 min using Turbula mixer. F tablets press 11 mm punch FFRE 450 mg table | 29.0 | Mouth: 10-15 S<br>Good tablets | Abrasion 1.0<br>Drop: 2.0 |
| Fluoxetine TMMS: 28.69<br>Advantose 100: 25.70<br>Pearlitol 400DC: 25.71<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-147/Feb. 4, 2002<br>250 g batch<br>Advantose 100/Perlitol 400DC (50/50) ratio | To investigate the combination of 2 polyols at different ratio and their effect on disintegration and friability. | ½ advantose, ½ Pearlitol, all MS, ½ Peqrlitol, ½ advantose, mix for 3 min. Add all Citric acid, all Acesu K, all syloid, all avicel, all L-HPC, all tangerine, mix for 5 min. Then pour all pruv and mix for 2 min using Turbula mixer. F tablets press 11 mm punch FFRE 450 mg table | 27.8 | Mouth: 10S<br>Good tablets | Abrasion 0.5<br>Drop: 1.9 |
| Fluoxetine TMMS: 28.69<br>Advantose 100: 12.85<br>Pearlitol 400DC: 38.56<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-148/Feb. 4, 2002<br>250 g batch<br>Advantose 100/Perlitol 400DC (25/75) ratio | To investigate the combination of 2 polyols at different ratio and their effect on disintegration and friability. | ½ advantose, ½ Pearlitol, all MS, ½ Pearlitol, ½ advantose, mix for 3 min. Add all Citric acid, all Acesu K, all syloid, all avicel, all L-HPC, all tangerine, mix for 5 min. Then pour all pruv and mix for 2 min using Turbula mixer. F tablets press 11 mm punch FFRE 450 mg table | 28.4 | Mouth: 15 S<br>Good tablets<br>No significant difference between 1242-147 | Abrasion 0.3<br>Drop: 0.5 |
| Fluoxetine TMMS: 28.69<br>Advantose 100: 38.56<br>Pearlitol 400DC: 12.85<br>Avicel PH 101: 15.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-149/Feb. 4, 2002<br>250 g batch<br>Advantose 100/Perlitol 400DC (75/25) ratio | To investigate the combination of 2 polyols at different ratio and their effect on disintegration and friability. | ½ advantose, ½ Pearlitol, all MS, ½ Pearlitol, ½ advantose, mix for 3 min. Add all Citric acid, all Acesu K, all syloid, all avicel, all L-HPC, all tangerine, mix for 5 min. Then pour all pruv and mix for 2 min using Turbula mixer. F tablets press 11 mm punch FFRE 450 mg table | 28.4 | Mouth: 10 S<br>Good tablets<br>Faster than 1242-147 & 148<br>1242-147 & 148 | Abrasion n: 0.5<br>Drop: 1.6 |

-continued

| | | | | | |
|---|---|---|---|---|---|
| Fluoxetine TMMS: 28.69<br>Pearlitol 400DC: 68.41<br>Citric acid: 1.0<br>AsesulK: 0.2<br>Tangerine: 0.2<br>Syloid: 0.5<br>Pruv: 1.0<br>Lot#/mfg date: 1242-151/Feb. 4, 2002<br>250 g batch | To compare the physical properties of pearlitol to advantols | ½ Pearlitol, all MS ½ Pearlitol, mix for 3 min. Add all Citric acid, all AcesuK, all syloid, all syloid, all tangerine, mix for 5 min. Then pour all pruv and mix for 2 min using Turbula mixer.<br>F tablets press 11 mm punch FFRE 450 mg table | 27.1 | Mouth: 35 S<br>Very slow | Abrasion 0.2<br>Drop: 0.3 |
| Fluoxetine TMMS: 28.69<br>Pearlitol 400DC: 51.41<br>Avicel PH 101: 15.0<br>Kollidon CL: 2.0<br>Citric acid: 1.0<br>AsesulK: 0.2<br>Tangerine: 0.2<br>Syloid: 0.5<br>Pruv: 1.0<br>Lot#/mfg date: 1242-152/Feb. 5, 2002<br>250 g batch | To evaluate the Kollidon CL and its effect on disintegration and friability in the pearlitol formulation. | ½ Pearlitol, all MS ½ Pearlitol, mix for 3 min. Add all Citric acid, all AcesuK, all syloid, all syloid, all avicel, all kollidon, all tangerine, mix for 5 min. Then pour all pruv and mix for 2 min using Turbula mixer.<br>F tablets press 11 mm punch FFRE 450 mg table | 33.9 | Mouth: 7-10 S<br>Very fast tablet | Abrasion 0.2<br>Drop: 0.6 |
| Fluoxetine TMMS: 28.69<br>Pearlitol 400Dc: 38.56<br>Advantose 100: 51.41<br>Avicel PH 101: 15.0<br>Kollidon CL: 2.0<br>Citric acid: 1.0<br>AsesulK: 0.2<br>Tangerine: 0.2<br>Syloid: 0.5<br>Pruv: 1.0<br>Lot#/mfg date: 1242-153/Feb. 4, 2002<br>250 g batch | To evaluate the Kollidon CL and its effect on disintegration and friability in the pearlitol formulation. | ½ advantose, ½ Pearlitol, all MS, ½ Pearlitol, ½ advantose, mix for 3 min. Add all Citric acid, all AcesuK, all syloid, all syloid, all avicel, all kollidon, all tangerine, mix for 5 min. Then pour all pruv and mix for 2 min using Turbula mixer.<br>F tablets press 11 mm punch FFRE 450 mg table | 30.8 | Mouth: 10 S<br>Very fast tablet no difference no 1242-152.<br>At 40N tablets disintegrate within 15 s | Abrasion 0.2<br>Drop: 0.2 |
| Fluoxetine TMMS: 28.69<br>Pearlitol 400DC: 56.41<br>Avicel PH 101: 10.0<br>Kollidon CL: 2.0<br>Citric acid: 1.0<br>AsesulK: 0.2<br>Tangerine: 0.2<br>Syloid: 0.5<br>Pruv: 1.0<br>Lot#/mfg date: 1242-154/Feb. 5, 2002<br>250 g batch | Optimize the avicel level | ½ Pearlitol, all MS ½ Pearlitol, mix for 3 min. Add all Citric acid, all AcesuK, all syloid, all syloid, all avicel, all kollidon, all tangerine, mix for 5 min. Then pour all pruv and mix for 2 min using Turbula mixer.<br>F tablets press 11 mm punch FFRE 450 mg table | 35.7 | Mouth: 15 S<br>Not as fast as 15% avicel | Abrasion 0.2<br>Drop: 0.3 |
| Fluoxetine TMMS: 28.69<br>Pearlitol 400DC: 42.31<br>Advantose 100: 51.41<br>Avicel PH 101: 15.0<br>Kollidon CL: 2.0<br>Citric acid: 1.0<br>AsesulK: 0.2<br>Tangerine: 0.2<br>Syloid: 0.5<br>Pruv: 1.0<br>Lot#/mfg date: 1242-155/Feb. 5, 2002<br>250 g batch | Optimize the avicel level | ½ advantose, ½ Pearlitol, all MS ½ Pearlitol, ½ advantose, mix for 3 min. Add all Citric acid, all AcesuK, all syloid, all syloid, all avicel, all kollidon, tangerine, mix for 5 min. Then pour all pruv and mix for 2 min using Turbula mixer.<br>F tablets press 11 mm punch FFRE 450 mg table | 26.7 | Mouth: 10-15 S<br>Not as fast 15% avicel | Abrasion 0.3<br>Drop: 0.8 |

-continued

| Formulation | Purpose | Procedure | Value | Mouth | Abrasion/Drop |
|---|---|---|---|---|---|
| Fluoxetine TMMS: 28.69<br>Pearlitol 400DC: 49.81<br>Advantose 100: 16.60<br>Kollidon CL: 2.0<br>Citric acid: 1.0<br>AsesulK: 0.2<br>Tangerine: 0.2<br>Syloid: 0.5<br>Pruv: 1.0<br>Lot#/mfg date: 1242-156/Feb. 5, 2002<br>250 g batch | Optimize the level of avicel | ½ advantose, ½ Pearlitol, all MS, ½ Pearlitol, ½ advantose mix for 3 min. Add all Citric acid, all AcesuK, all syloid, all syloid, all kollidon, tangerine, mix for 5 min. Then pour all pruv and mix for 2 min using Turbula mixer. F tablets press 11 mm punch FFRE 450 mg table | 21.6 | Mouth: 35 S Very slow | Abrasion 0.2<br>Drop: 0.3 |
| Fluoxetine TMMS: 28.69<br>Pearlitol 400DC: 49.41<br>Avicel PH 101: 15.0<br>Kollidon CL: 2.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-157/Feb. 6, 2002<br>250 g batch | To evalute the combination of Kollidon CL/L0HPC and their synergetic effect on disintegration and friability formulation. | ½ Pearlitol, all MS ½ Pearlitol, mix for 3 min. Add all Citric acid, all AcesuK, all syloid, all syloid, all kollidon, all - HPC, all tangerine, mix for 5 min. Then pour all pruv and mix for 2 min using Turbula mixer. F tablets press 11 mm punch FFRE 450 mg table | 29.4 | Mouth: 10 S Very fast tablet, no difference between 1242-154 & 140 batches | Abrasion 0.4<br>Drop: 0.6 |
| Fluoxetine TMMS: 28.69<br>Pearlitol 400DC: 37.06<br>Advantose 100: 12.35<br>Avicel PH 101: 15.0<br>Kollidon CL: 2.0<br>L-HPC 11: 2.0<br>Citric acid: 1.0<br>AsesulK: 0.2<br>Tangerine: 0.2<br>Syloid: 0.5<br>Pruv: 1.0<br>Lot#/mfg date: 1242-158/Feb. 6, 2002<br>250 g batch | To evaluate the combination of Kollidon CL/L0HPC and their synergetic effect on disintegration and friability formulation. | ½ advantose, ½ Pearlitol, all MS, ½ Pearlitol, ½ advantose, mix for 3 min. Add all Citric acid, all AcesuK, all syloid, all syloid, all kollidon, all tangerine, mix for 5 min. Then pour all pruv and mix for 2 min using Turbula mixer. F tablets press 11 mm punch FFRE 450 mg table | 33.1 | Mouth: 12-15 S Good tablets | Abrasion 0.3<br>Drop: 0.6 |
| Fluoxetine TMMS: 28.69<br>Lab 3038: 51.41<br>Avicel PH 101: 15.0<br>Kollidon CL: 2.0<br>Citric acid: 1.0<br>AsesulK: 0.2<br>Tangerine: 0.2<br>Syloid: 0.5<br>Pruv: 1.0<br>Lot#/mfg date: 1242-159/Feb. 6, 2002<br>250 g batch | To evaluate alternative polyols with Kollidon and their effect on disintegration | ½ lab, all MS ½ lab, mix for 3 min. Add all Citric acid, all AcesuK, all syloid, all syloid, all kollidon, all tangerine, mix for 5 min. Then pour all pruv and mix for 2 min using Turbula mixer. F tablets press 11 mm punch FFRE 450 mg table | 25.3 | Mouth: 10 S Good tablets | Abrasion 0.6<br>Drop: 2.0 |
| Fluoxetine TMMS: 28.69<br>Lab 3038: 68.41<br>Avicel PH 101: 15.0<br>L-HPC 11: 2.0<br>Citric acid: 1.0<br>AsesulK: 0.2<br>Tangerine: 0.2<br>Syloid: 0.5 | To evaluate alternative polyols with L-HPC and their effect on disintegration. | ½ lab, all MS ½ lab, mix for 3 min. Add all Citric acid, all AcesuK, all syloid, all syloid, all HPC, all tangerine, mix for 5 min. Then pour all pruv and mix for 2 min using Turbula mixer. | 32.4 | Mouth: 20 S | Abrasion 0.2<br>Drop: 0.8 |

-continued

| Pruv: 1.0 | F tablets press |
| Lot#/mfg date: | 11 mm punch FFRE |
| 1242-160/Feb. 6, 2002 | 450 mg table |
| 250 g batch | |

Additional Non-Floss Formulations

| Formulation Lot# | Objective | Mixing procedure & Equipment Used | Hardness (N) | Disintegration time | Friability % | Dissolution % |
|---|---|---|---|---|---|---|
| Fluoxetine TMMS: 28.69<br>Pearlitol 400DC: 58.41<br>Kolidon XL: 10<br>Citric acid: 1.0<br>AsesulK: 0.2<br>Syloid: 0.5<br>Tangerine: 0.2<br>Pruv: 1.0<br>Lot#1242-117 | Investigate high level of Kollidon XL for fast disintegration using high compression. | ½ Pearl 400DC, all MS ½ pearlitol 400DC, mix for 3 min. Add all Citric acid, all AcesuK, all syloid, all Kollidon, all tangerine, mix for 5 min. Then pour all pruv and mix for 2 min using Turbula mixer. Piccola tablets press 11 mm punch FFRE | 32 | Mouth: 10 S | Abrasion 0.3<br>Drop: 2.1 | |
| Fluoxetine TMMS: 28.69<br>Parteck M200: 58.41<br>Kolidon XL: 10<br>Citric acid: 1.0<br>AsesulK: 0.2<br>Syloid: 0.5<br>Tangerine: 0.2<br>Pruv: 1.0<br>Lot#1242-118 | Evaluate different mannitol from different suppliers. | ½ Parteck M200, all MS, ½ Parteck M200 mix for 3 min. Add all Citric acid, all AcesuK, all syloid, all Kollidon, all tangerine, mix for 5 min. Then pour all pruv and mix for 2 min. using Turbula mixer. Piccola tablets press 11 mm punch FFRE | 22.2 | Mouth: 10 S | Abrasion 1.4<br>Drop: 4.1 | |
| Fluoxetine TMMS: 28.69<br>Parteck M300: 58.41<br>Kolidon XL: 10<br>Citric acid: 1.0<br>AsesulK: 0.2<br>Syloid: 0.5<br>Tangerine: 0.2<br>Pruv: 1.0<br>Lot#1242-119 | Evaluate different mannitol from different suppliers. | ½ Parteck M300, all MS, ½ Parteck M300, mix for 3 min. Add all Citric acid, all Acesu K, all syloid, all Kollidon, all tangerine, mix for 5 min. Then pour all pruv and mix for 2 min. using Turbula mixer. Piccola tablets press 11 mm punch FFRE | 30.0 | Mouth: 10 S | Abrasion 0.8<br>Drop: 3.0 | |
| Fluoxetine TMMS: 28.69<br>Pearlitol 400DC: 48.41<br>Kolidon XL: 20<br>Citric acid: 1.0<br>AsesulK: 0.2<br>Syloid: 0.5 | Increase the Kollidon XL from 10% to 20% to determine the | ½ Pearlitol 400DC, all MS, ½ Pearlitol 400DC, mix for 3 min. Add all Citric acid, all Acesu K, all | 27.0 | Mouth: 10 S | Abrasion 0.4<br>Drop: 2.3 | |

-continued

| | | | | | |
|---|---|---|---|---|---|
| Tangerine: 0.2<br>Pruv: 1.0<br>Lot#1242-120 | effect of disintegrant concentration on disintegration. time | syloid, all Kollidon, all tangerine, mix for 5 min. Then pour all pruv and mix for 2 min. using Turbula mixer. Piccola tablets press 11 mm punch FFRE | | | |
| FluoxetineTMMS: 28.69<br>Pearlitol 400DC: 48.41<br>L-HPC11: 20<br>Citric acid: 1.0<br>AsesulK: 0.2<br>Syloid: 0.5<br>Tangerine: 0.2<br>Pruv: 1.0<br>Lot#1242-123 | Investigate alternative disintegrant like L-HPC11 | ½ Pearlitol 400DC, all MS, ½ Pearlitol 400DC, mix for 3 min. Add all Citric acid, all Acesu K, all syloid, all L-HPC, all tangerine, mix for 5 min. Then pour all pruv and mix for 2 min. using Turbula mixer. Piccola tablets press 11 mm punch FFRE | 16.2 | Mouth 20 S, at 20 and 30 N tables very slow to disintegrate | Abrasion 14.8<br>Drop: powder collection |
| Fluoxetine TMMS: 28.69<br>Pearlitol 400DC: 48.41<br>Avicel PH 101: 16.0<br>L-HPC 11: 4.0<br>Citric acid: 1.0<br>AsesulK: 0.2<br>Syloid: 0.5<br>Tangerine: 0.2<br>Pruv: 1.0<br>Lot#1242-124<br>Avicel PH101/L-HPC11 ratio (80/20) | Introduce microcrystalline cellulose as a wicking and dispersin agent to improve the disintegration of the tablets. | ½ Pearlitol 400DC, all MS, ½ Pearlitol 400DC, mix for 3 min. Add all Citric acid, all Acesu K, all syloid, all avicel, all L-HPC, all tangerine, mix for 5 min.. Then pour all pruv and mix for 2 min using Turbula mixer. Piccola tablets press 11 mm punch FFRE | 30.0 | Mouth: 10 S | Abrasion 0.2<br>Drop: 0.8 |
| Fluoxetine TMMS: 28.69<br>Pearlitol 400DC: 48.41<br>Avicel PH 101: 18.0<br>L-HPC 11: 2.0<br>Citric acid: 1.0<br>AsesulK: 0.2<br>Syloid: 0.5<br>Tangerine: 0.2<br>Pruv: 1.0<br>Lot#1242-125<br>Avicel PH 101/L-HPC11 ratio (90/10) | Evaluate different ratio of avicel PH 101/L-HPC 11 to determine which excipient affect more the disintegration in the mouth | ½ Pearlitol 400DC, all MS, ½ Pearlitol 400DC mix for 3 min. Add all Citric acid, all Acesu K, all syloid, all avicel, all L-HPC, all tangerine, mix for 5 min. Then pour all pruv and mix for 2 min using Turbula mixer. Piccola tablets press 11 mm punch FFRE | 34.0 | Mouth: 10 S | Abrasion 0.2<br>Drop: 0.8 |

| | | | | | |
|---|---|---|---|---|---|
| Fluoxetine TMMS: 28.69<br>Pearlitol 400DC: 48.41<br>Avicel PH 101: 14.0<br>L-HPC 11: 6.0<br>Citric acid: 1.0<br>AsesulK: 0.2<br>Syloid: 0.5<br>Tangerine: 0.2<br>Pruv: 1.0<br>Lot#1242-129<br>Avicel PH 101/L-HPC11 ratio (70/30) | Evaluate different ratio of avicel PH 101/L-HPC 11 to determine which excipient affect more the disintegration in the mouth | ½ Pearlitol 400DC, all MS,<br>½ Pearlitol 400DC, mix for 3 min. Add all Citric acid, all Acesu K, all syloid, all avicel, all L-HPC, all tangerine, mix for 5 min. Then pour all pruv and mix for 2 min using Turbula mixer. Piccola tablets press 11 mm punch FFRE | 34.0 | Mouth: 10 S | Abrasion 0.2<br>Drop: 1.0 |
| Fluoxetine TMMS: 28.69<br>Pearlitol 400DC: 48.41<br>Avicel PH 101: 16.0<br>Kollidon XL: 4.0<br>Citric acid: 1.0<br>AsesulK: 0.2<br>Syloid: 0.5<br>Tangerine: 0.2<br>Pruv: 1.0<br>Lot#1242-126<br>Avicel PH 101/Kollidon ratio (80/20) | Comparative study of disintegration time of avicel PH 101/L-HPC11 formulation versus avicel PH 101/Kollidon XL | ½ Pearlitol 400DC, all MS,<br>½ Pearlitol 400DC, mix for 3 min. Add all Citric acid, all Acesu K, all syloid, all avicel, all Killidon, all tangerine, mix for 5 min. Then pour all pruv and mix for 2 min using Turbula mixer. Piccola tablets press 11 mm punch FFRE | 34.0 | Mouth: 10 S | Abrasion 0.1<br>Drop: 1.5 |
| Fluoxetine TMMS: 28.69<br>Pearlitol 400DC: 48.41<br>Avicel PH 101: 4.0<br>Kollidon XL: 16.0<br>Citric acid: 1.0<br>AsesulK: 0.2<br>Syloid: 0.5<br>Tangerine: 0.2<br>Pruv: 1.0<br>Lot#1242-127<br>Avicel PH 101/Kollidon ratio (20/80) | Comparative study of disintegration time of avicel PH 101/L-HPC11 formulation versus avicel PH 101/Kollidon | ½ Pearlitol 400DC, all MS,<br>½ Pearlitol 400DC, mix for 3 min. Add all Citric acid, all Acesu K, all syloid, all avicel, all Kollidon, all tangerine, mix for 5 min. Then pour all pruv and mix for 2 min using Turbula mixer. Piccola tablets press 11 mm punch FFRE | 31-37 | Mouth: 10 S | Abrasion 0.04<br>Drop: 1.6 |
| Fluoxetine TMMS: 28.69<br>Pearlitol 400DC: 52.41<br>Kollidon XL: 16.0<br>Citric acid: 1.0<br>AsesulK: 0.2<br>Syloid: 0.5<br>Tangerine: 0.2<br>Pruv: 1.0<br>Lot#1242-130 | Comparative study of disintegration time of 16% Kollidon to 10 and 20% | ½ Pearlitol 400DC, all MS,<br>½ Pearlitol 400DC, mix for 3 min. Add all Citric acid, all Acesu K, all syloid, all Kollidon, all tangerine, mix for 5 min. Then pour all pruv and mix for 2 min using | 33.3 | Mouth: 10 S | Abrasion 1.0<br>Drop: 2.5 |

-continued

| | | Turbula mixer. Piccola tablets press 11 mm punch FFRE. | | | |
|---|---|---|---|---|---|
| FluoxetineTMMS: 28.69<br>Pearlitol 400DC: 26.25<br>Avicel PH 101: 26.25<br>L-HPC: 16<br>Citri ca cid: 1.0<br>AsesulK: 0.2<br>Syloid: 0.5<br>Tangerine: 0.2<br>Pruv: 1.0<br>Lot#1242-131 | Increase the level of avicel to improve the disintegration time. Avicel is porous and therefore, it absorbs lot of water which helps the swelling of L-HPC | ½ Pearlitol 400DC, all MS, ½ Pearlitol 400DC, mix for 3 min. Add all Citric acid, all Acesu K, all syloid, all avicel, all L-HPC, all tangerine, mix for 5 min. Then pour all pruv and mix for 2 min using Turbula mixer. F tablets press 11 mm punch FFRE. | 29.4 | Mouth: 10 S | Abrasion 1.7<br>Drop: 1.8 |
| FluoxetineTMMS: 28.69<br>Pearlitol 400DC: 26.25<br>Avicel PH 101: 26.25<br>Kolidon XL: 16<br>Citri ca cid: 1.0<br>AsesulK: 0.2<br>Syloid: 0.5<br>Tangerine: 0.2<br>Pruv: 1.0<br>Lot#1242-132 | Same objective as 1242-131, except Kollidon was used. | ½ Pearlitol 400DC, all MS, ½ Pearlitol 400DC, mix for 3 min. Add all Citric acid, all Acesu K, all syloid, all avicel, all Kollidon, all tangerine, mix for 5 min. Then pour all pruv and mix for 2 min. using Turbula mixer. F tablets press 11 mm punch FFRE. | 29.7 | Mouth: 10 S | Abrasion 0.3<br>Drop: 0.8 |
| Ireland Formulation EXP 988 | Enapril FD tablets 36 mg | | 26 | Mouth: 10 S | Abrasion 2.5<br>Drop: 13.5 |
| FluoxetineTMMS: 28.69<br>Pearlitol 400DC: 54.41<br>Avicel PH 101:12<br>L-HPC: 2<br>Citri ca cid: 1.0<br>AsesulK: 0.2<br>Syloid: 0.5<br>Tangerine: 0.2<br>Pruv: 1.0<br>Lot#1242-133 | Study the effect of avicel on the tablets formulation at differents level 12% and 6% as results of lot 1242-125 | ½ Pearlitol 400DC, all MS, ½ Pearlitol 400DC, mix for 3 min. Add all Citric acid, all Acesu K, all syloid, all avicel, all L-HPC, all tangerine, mix for 5 min. Then pour all pruv and mix for 2 min using Turbula mixer. F tablets press 11 mm punch FFRE. | 28.3 | Mouth: 15 to 20 S | Abrasion 0.3<br>Drop: 0.3 |
| FluoxetineTMMS: 28.69<br>Pearlitol 400DC: 60.41<br>Avicel PH 101: 6<br>L-HPC: 2<br>Citri ca cid: 1.0 | To improve the mouth feel and gritty taste of | ½ Pearlitol 400DC, all MS, ½ Pearlitol 400DC, mix for 3 min. Add all Citric acid, | 28.1 | Mouth: 20 S slow compared to 1242-133 | Abrasion 0.4<br>Drop: 0.4 |

-continued

| | | | | | |
|---|---|---|---|---|---|
| AsesulK: 0.2<br>Syloid: 0.5<br>Tangerine: 0.2<br>Pruv: 1.0<br>Lot#1242-134 | the tablets. Avicel was reduced from 18% to 12% by keeping L-HPC 11 to 2% level in tablets formulation | all Acesu K, all syloid, all avicel, all L-HPC, all tangerine, mix for 5 min. Then pour all pruv and mix for 2 min using Turbula mixer. F tablets press 11 mm punch FFRE. | | | |
| FluoxetineTMMS: 28.69<br>Pearlitol 400DC: 51.41<br>Avicel PH 101:15<br>L-HPC: 2<br>Citri ca cid: 1.0<br>AsesulK: 0.2<br>Syloid: 0.5<br>Tangerine: 0.2<br>Pruv: 1.0<br>Lot#1242-135 | As results of 1242-125 and 1242-133 on the tablets disintegration, is been found that the lot 1242-125 gave better disintegration which the level of Avicel was increased to 15% | ½ Pearlitol 400DC, all MS, ½ Pearlitol 400DC, mix for 3 min. Add all Citric acid, all Acesu K all syloid, all avicel, all L-HPC, all tangerine, mix for 5 min. Then pour all pruv and mix for 2 min using Turbula mixer. F tablets press 11 mm punch FFRE. | 29.5 | Mouth: 10 S | Abrasion 0.3<br>Drop: 0.3 |
| FluoxetineTMMS: 28.69<br>Pearlitol 400DC: 53.41<br>Avicel PH 101: 15<br>Citri ca cid: 1.0<br>AsesulK: 0.2<br>Syloid: 0.5<br>Tangerine: 0.2<br>Pruv: 1.0<br>Lot#1242-136 | Evaluate the used of avicel alone in the tablets formulation. To determine the effect of the disintegration while L-HPC11 was removed. | ½ Pearlitol 400DC, all MS, ½ Pearlitol 400DC, mix for 3 min. Add all Citric acid, all Acesu K, all syloid, all avicel, all tangerine, mix for 5 min. Then pour all pruv and mix for 2 min using Turbula mixer. F tablets press 11 mm punch FFRE. | 27.5 | Mouth: 20 S | Abrasion 0.2<br>Drop: 0.4 |
| FluoxetineTMMS: 28.69<br>Pearlitol 400DC: 51.41<br>Prosolv90: 15<br>L_HPC 11: 2<br>Citri ca cid: 1.0<br>AsesulK: 0.2<br>Syloid: 0.5<br>Tangerine: 0.2<br>Pruv: 1.0<br>Lot#1242-137 | Investigate another disintegrant Prosolv90 to study the disintegration properties and compare its effectiveness with avicel in a direct compaction. | ½ Pearlitol 400DC, all MS, ½ Pearlitol 400DC, mix for 3 min. Add all Citric acid, all Acesu K, all syloid, all Prosolv90, all L_HPC11, all tangerine, mix for 5 min. Then pour all pruv and mix for 2 min using Turbula mixer. F tablets press 11 mm punch FFRE. | 28.3 | Mouth: 10 S better disint than 1242-125 | Abrasion 0.2<br>Drop: 0.4 |

Preferred Oormulations Based on Directly Compressible Inorganic Salts, Alone or in Combination with a Cellulose Derivative:

The present preferred illustrative embodiments of the invention relate to the introduction of directly compressible inorganic salt with a cellulose derivative.

|  | % |
|---|---|
| Formulation I: This formulation is based on an excipient mass containing a misture of dibasic calcium phosphate dihydrate (Emcompress) and microcrystalline cellulose (Avicel). | |
| FluoxetineTMMS*: | 28.69 |
| Pearlitol 400DC | 36.31 |
| Emcompress: | 12.10 |
| Avicel PH 101: | 15.00 |
| L-HPC LH-11: | 2.00 |
| XL Kollidon: | 2.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation II: This formulation is based on an excipient mass wherein mannitol is substituted with the dicalcium phosphate dihydrate. | |
| Fluoxetine TMMS*: | 28.69 |
| Emcompress: | 48.41 |
| Avicel PH 101: | 15.00 |
| XL Kollidon: | 2.00 |
| L-HPC LH-11: | 2.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation III: This formulation is based on an excipient mnass wherein microcrystalline cellulose (Avicel) is substituted with the dicalcium phosphate dihydrate (Emcompress) | |
| Fluoxetine TMMS*: | 28.69 |
| Pearlitol 400DC: | 48.41 |
| Emcompress: | 15.00 |
| L-HPC LH-11: | 2.00 |
| XL Kollidon: | 2.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation IV: This formulation is based on an excipient mass containing a combination of Pearlitol 400DC/dicalcium phosphate dihydrate at ratio 75/25 | |
| Fluoxetine TMMS*: | 28.69 |
| Pearlitol 400DC: | 36.69 |
| Emcompress: | 12.10 |
| Avicel PH 101: | 15.00 |
| XL Kollidon: | 2.00 |
| L-HPC LH-11: | 2.00 |
| Acesulfame K: | 0.20 |
| Magnasweet 100: | 0.20 |
| Tangerine Flavor: | 0.50 |
| Citric Acid anhydrous: | 1.50 |

-continued

|  | % |
|---|---|
| Syloid 244FP: | 0.50 |
| Pruv: | 1.00 |
| Formulation V: | |
| Fluoxetine TMMS*: | 28.69 |
| Pearlitol 400DC: | 36.31 |
| Emcompress: | 17.10 |
| Avicel PH 101: | 10.00 |
| XL Kollidon: | 2.00 |
| L-HPC LH-11: | 2.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation VI: This formulation is based on an excipient mass containing a combination of low level of Avicel with Emcompress. | |
| Fluoxetine TMMS*: | 28.69 |
| Pearlitol 400DC: | 43.81 |
| Emcompress: | 12.10 |
| Avicel PH 101: | 7.50 |
| XL Kollidon: | 2.00 |
| L-HPC LH-11: | 2.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation VII: | |
| Fluoxetine TMMS*: | 28.69 |
| Pearlitol 400DC: | 48.41 |
| Emcompress: | 7.50 |
| Avice PH 101: | 7.50 |
| XL Kollidon: | 2.00 |
| L-HPC LH-11: | 2.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation VIII: This formulation illustrates how the introduction of Clay (magnabrite) in tablet formulation according to the invention allows for covering the unpleasant and gritty taste of the microspheres and therevy improve the patient's ability to to swallow a tablet based on this formulation. | |
| Fluoxetine TMMS*: | 28.69 |
| Pearlitol 400DC: | 43.81 |
| Emcompress: | 12.10 |
| Avicel PH 101: | 6.50 |
| XL Kollidon: | 2.00 |
| L-HPC LH-11: | 2.00 |
| Magnabrite F: | 1.00 |
| Acesulfame K: | 0.20 |
| Magnasweet 100: | 0.20 |
| Tangerine Flavor: | 0.50 |
| Citric Acid anhydrous: | 1.50 |
| Syloid 244FP: | 0.50 |
| Pruv: | 1.00 |
| Formulation IX: | |
| Fluoxetine TMMS*: | 28.69 |
| Pearlitol 400DC: | 43.81 |
| Emcompress: | 12.10 |
| Avicel PH 101: | 7.50 |
| XL Kollidon: | 2.00 |
| Magnabrite F: | 2.00 |
| Acesulfame K: | 0.20 |
| Magnasweet 100: | 0.20 |
| Tangerine Flavor: | 0.50 |

-continued

|  | % |
| --- | --- |
| Citric Acid anhydrous: | 1.50 |
| Syloid 244FP: | 0.50 |
| Pruv: | 1.00 |
| Formulation X: | |
| Fluoxetine TMMS*: | 28.69 |
| Pearlitol 400DC: | 43.81 |
| Emcompress: | 12.10 |
| Avicel PH 101: | 7.50 |
| Magnabrite F: | 4.00 |
| AcesulfameK: | 0.20 |
| Magnasweet100: | 0.20 |
| Tangerine Flavor: | 0.50 |
| Citric Acid anhydrous: | 1.50 |
| Syloid 244FP: | 0.50 |
| Pruv: | 1.00 |

*Note:
TMMS = Taste Masked Microspheres. Fluoxetine was used as a model drug, but these formulas cover the use of any coated or uncoated CEFORM ™ Microsphere.
Reasonable variations, such as those which would occur to a skilled artisan, can be made herein without departing from the scope of the invention.

What is claimed is:

1. A direct compression quick dissolve oral dosage form optionally comprising a super disintegrant, comprising:
   (a) a drug-containing microparticle, and
   (b) an excipient mass comprising:
      (i) from 0% to about 3% by weight of a super disintegrant,
      (ii) at least one of a directly compressible inorganic salt, a cellulose derivative, and a mixture thereof; and
      (iii) at least one directly compressible filler;
   wherein said oral dosage form is a fast dissolving oral dosage form that dissolves in the mouth in less than about 40 seconds, has a friability of less than about 1%, and is manufactured by direct compression processing.

2. The oral dosage form of claim 1, comprising 0% by weight of a super disintegrant.

3. The oral dosage form of claim 1, wherein the drug-containing microparticle comprises at least one drug, and a combination of at least one solubilizer and at least one spheronization aid.

4. The oral dosage form of claim 1, wherein the excipient mass is comprised of about 50% directly compressible inorganic salt and about 50% cellulose derivative.

5. The oral dosage form of claim 1, wherein the excipient mass comprises at least one directly compressible inorganic salt selected from the group consisting of directly compressible dibasic calcium phosphate dihydrate, magnesium aluminum silicate NF, and mixtures thereof.

6. The oral dosage form of claim 1, wherein the excipient mass comprises a linear polyol.

7. The oral dosage form of claim 1, wherein the excipient mass comprises a directly compressible polyol.

8. The oral dosage form of claim 1, wherein the excipient mass further comprises mannitol; xylitol or a mixture thereof.

9. The oral dosage form of claim 1, wherein the excipient mass further comprises lactose, maltose, sucrose or a mixture thereof.

10. The oral dosage form of claim 1, wherein the drug-containing microparticles are liquiflash particles, and the drug-containing microparticles and the excipient mass are combined in proportions selected such that the drug remains within the liquiflash particles when the composition is compressed to obtain a dosage form having a hardness of from about 20 N to about 50 N.

11. The oral dosage form of claim 1, wherein the drug-containing microparticles particles are coated.

12. The oral dosage form of claim 1, wherein the drug-containing microparticles particles are coated with at least one taste-masking coating.

13. The oral dosage form of claim 11, wherein the coating contains at least one cellulosic polymer.

14. The oral dosage form of claim 11, wherein the coating comprises a polymethacrylate polymer.

15. The oral dosage form of claim 1, which dissolves in the mouth in less than about 30 seconds.

16. The oral dosage form of claim 1, wherein said oral dosage form dissolves in the mouth in less than about 30 seconds and comprises from about 5% to about 45% by weight of drug-containing microparticles, and from about 25% to about 85% by weight of an excipient mass, wherein the excipient mass contains less than about 2.5% by weight of a super disintegrant.

17. The oral dosage form of claim 1, comprising from about 5% to about 20% by weight of microcrystalline cellulose.

18. The oral dosage form of claim 1, comprising from about 15% to about 18% by weight of microcrystalline cellulose.

19. The oral dosage form of claim 1, wherein the super disintegrant is present in an amount of less than about 2.2% by weight.

20. The oral dosage form of claim 1, wherein the super disintegrant is present in an amount of less than about 2.0% by weight.

21. The oral dosage form of claim 1, wherein the super disintegrant is present at a proportion of less than about 1.5% by weight.

22. The oral dosage form of claim 1, wherein the drug-containing microparticles comprise a drug selected from the group consisting of fluoxetine; paroxetine; zolpidem; tevenen; Cox-2 inhibitor; Ace inhibitor; a calcium channel blocker, and mixtures thereof.

23. The oral dosage form of claim 1, wherein the drug-containing microparticles comprise a drug selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, $H_2$-antagonists, anti-uricemic drugs and mixtures thereof.

24. The oral dosage form of claim 1, which dissolves in the mouth in less than about 15 seconds.

25. The oral dosage form of claim 1, wherein the drug-containing microparticles comprise zolpidem.

26. The oral dosage form of claim 1, wherein the drug-containing microparticles comprise a pharmaceutically acceptable salt of zolpidem.

27. The oral dosage form of claim 25, wherein the drug-containing microparticles further comprise glyceryl stearate.

28. The oral dosage form of claim 26, wherein the drug-containing microparticles further comprises glyceryl stearate.

29. The oral dosage form of claim 27, wherein the drug-containing microparticle further comprises hydroxypropylmethylcellulose.

30. The oral dosage form of claim 28, wherein the drug-containing microparticle further comprises hydroxypropylmethylcellulose.

31. The oral dosage form of claim 1, wherein the excipient mass comprises a cellulose derivative.

32. The oral dosage form of claim 31, wherein the excipient mass comprises low substituted hydroxypropyl cellulose.

33. The oral dosage form of claim 25, wherein the excipient mass comprises low substituted hydroxypropyl cellulose.

34. The oral dosage form of claim 26, wherein the excipient mass comprises low substituted hydroxypropyl cellulose.

35. The oral dosage form of claim 25, wherein the excipient mass comprises microcrystalline cellulose.

36. The oral dosage form of claim 26, wherein the excipient mass comprises microcrystalline cellulose.

37. The oral dosage form of claim 25, wherein the excipient mass comprises crospovidone.

38. The oral dosage form of claim 26, wherein the excipient mass comprises crospovidone.

39. The oral dosage form of claim 25, wherein the excipient mass comprises microcrystalline cellulose, crospovidone, and low substituted hydroxypropyl cellulose.

40. The oral dosage form of claim 26, wherein the excipient mass comprises microcrystalline cellulose, crospovidone, and low substituted hydroxypropyl cellulose.

41. The oral dosage form of claim 39, wherein the excipient mass further comprises mannitol.

42. The oral dosage form of claim 40, wherein the excipient mass further comprises mannitol.

43. The oral dosage form of claim 41, wherein the excipient mass further comprises a sweetener.

44. The oral dosage form of claim 42, wherein the excipient mass further comprises a sweetener.

45. The oral dosage form of claim 1, wherein the directly compressible filler comprises a directly compressible polyol.

46. The oral dosage form of claim 45, wherein the directly compressible polyol comprises at least one of mannitol, sorbitol, xylitol, or a mixture thereof.

47. The oral dosage form of claim 1, wherein the directly compressible filler comprises at least one of lactose, maltose, sucrose, dextrose, or a mixture thereof.

48. The oral dosage form of claim 1, wherein said oral dosage form is a fast dissolving oral dosage form that dissolves in the mouth in less than 30 seconds.

* * * * *